(12) United States Patent
Zhang et al.

(10) Patent No.: US 11,174,320 B2
(45) Date of Patent: *Nov. 16, 2021

(54) HER3 SPECIFIC MONOCLONAL ANTIBODIES FOR DIAGNOSTIC AND THERAPEUTIC USE

(71) Applicant: THE BOARD OF REGENTS OF THE UNIVERSITY OF TEXAS SYSTEM, Austin, TX (US)

(72) Inventors: Ningyan Zhang, Houston, TX (US); Zhiqiang An, Houston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 62 days.

This patent is subject to a terminal disclaimer.

(21) Appl. No.: 16/441,350

(22) Filed: Jun. 14, 2019

(65) Prior Publication Data
US 2020/0055954 A1    Feb. 20, 2020

Related U.S. Application Data

(60) Continuation of application No. 15/643,690, filed on Jul. 7, 2017, now Pat. No. 10,358,501, which is a division of application No. 14/774,808, filed as application No. PCT/US2014/025446 on Mar. 13, 2014, now Pat. No. 9,725,520.

(60) Provisional application No. 61/782,770, filed on Mar. 14, 2013.

(51) Int. Cl.
| C07K 16/32 | (2006.01) |
| G01N 33/574 | (2006.01) |
| A61F 7/10 | (2006.01) |
| A61K 39/395 | (2006.01) |
| A61K 45/06 | (2006.01) |
| A61N 5/10 | (2006.01) |
| A61K 39/00 | (2006.01) |

(52) U.S. Cl.
CPC .......... *C07K 16/32* (2013.01); *A61F 7/10* (2013.01); *A61K 39/39558* (2013.01); *A61K 45/06* (2013.01); *A61N 5/10* (2013.01); *G01N 33/57484* (2013.01); *G01N 33/57492* (2013.01); *A61K 2039/505* (2013.01); *C07K 2317/14* (2013.01); *C07K 2317/24* (2013.01); *C07K 2317/55* (2013.01); *C07K 2317/565* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,566,770 B2 | 7/2009 | Watkins et al. |
| 8,119,147 B2 | 2/2012 | Emery et al. |
| 8,333,966 B2 | 12/2012 | Tan et al. |
| 9,725,520 B2 | 8/2017 | Zhang et al. |
| 10,358,501 B2 | 7/2019 | Zhang et al. |
| 2008/0124345 A1* | 5/2008 | Rothe .............. C07K 16/2863 424/174.1 |
| 2010/0166773 A1 | 7/2010 | Marks et al. |
| 2013/0259867 A1 | 10/2013 | Amler |

FOREIGN PATENT DOCUMENTS

| CN | 1541109 A | 10/2004 |
| CN | 102822201 A | 12/2012 |
| EP | 0531472 | 8/2013 |
| WO | WO 2003/013602 | 2/2003 |
| WO | WO 2011/044311 | 4/2011 |
| WO | WO 2011/076683 | 6/2011 |
| WO | WO 2012/044612 | 4/2012 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79): 18294-18302, 2011).*
Extended European Search Report issued in European Application No. 14772555.0, dated Aug. 17, 2016.
International Preliminary Report on Patentability issued in International Application No. PCT/US2014/025446, dated Sep. 15, 2015.
International Search Report and Written Opinion issued in International Application No. PCT/US2014/025446, dated Sep. 4, 2014.
Jura et al., "Structural analysis of the catalytically inactive kinase domain of the human EGF receptor 3." *Proceedings of the National Academy of Sciences* 106.51 (2009): 21608-21613.
Lin et al., "Improved affinity of a chicken single-chain antibody to avian infectious bronchitis virus bv site-directed mutagenesis of complementarity-determining region H3", *Aifrican J. Biotechnol.*, 10(79):18294-18302, 2011.
Mariuzza, R. A., and S. Phillips. "E. V. 85 Poljak, R. J.(1987)." *Anna. Ree. Biophys. Biophys. Chem* 16: 139-159.
McCarthy, Barry J., and Amanda S. Hill. "Altering the fine specificity of an anti-Legionella single chain antibody by a single amino acid insertion." *Journal of immunological methods* 251.1 (2001): 137-149.
NCBI, GenBank Accession No. AAB18983.1, dated May 14, 2001.
NCBI, GenBank Accession No. AAF98336.1, dated Aug. 10, 2000.
NCBI, GenBank Accession No. AAK84193.1, dated Jul. 2, 2003.
NCBI, GenBank Accession No. AAM44740.1, dated May 30, 2002.

(Continued)

*Primary Examiner* — Nelson B Moseley, II
(74) *Attorney, Agent, or Firm* — Parker Highlander PLLC

(57) ABSTRACT

Isolated or recombinant anti-HER3 monoclonal antibodies are provided. In some cases, antibodies of the embodiments can be used for the detection, diagnosis and/or therapeutic treatment of human diseases, such as cancer.

20 Claims, 12 Drawing Sheets

Specification includes a Sequence Listing.

(56) References Cited

OTHER PUBLICATIONS

NCBI, GenBank Accession No. AAO06483.1, dated Jan. 3, 2003.
NCBI, GenBank Accession No. AAO06509.1, dated Jan. 3, 2003.
NCBI, GenBank Accession No. AAP43486.1, dated Jan. 7, 2004.
NCBI, GenBank Accession No. AAQ72927.1, dated Jan. 7, 2004.
NCBI, GenBank Accession No. AAR91824.1, dated Jan. 18, 2004.
NCBI, GenBank Accession No. ACN43616.1, dated Mar. 7, 2009.
NCBI, GenBank Accession No. AGB75995.1, dated Jan. 9, 2013.
NCBI, Reference Sequence No. XP_629704.1, dated Jan. 29, 2010.
Office communication issued in Chinese Application No. 201480015195.5, dated May 3, 2018.

* cited by examiner

FIGS. 8A-B

HER3 SPECIFIC MONOCLONAL ANTIBODIES FOR DIAGNOSTIC AND THERAPEUTIC USE

This application is a continuation of U.S. patent application Ser. No. 15/643,690, filed Jul. 7, 2017, which is a division of U.S. patent application Ser. No. 14/774,808, filed Sep. 11, 2015, as a national phase application under 35 U.S.C. § 371 of International Application No. PCT/US2014/025,446, filed Mar. 13, 2014, which claims the benefit of U.S. Provisional Patent Application No. 61/782,770, filed Mar. 14, 2013, the entirety of each of which is incorporated herein by reference.

INCORPORATION OF SEQUENCE LISTING

The sequence listing that is contained in the file named "UTSHP0295USC1_ST25.txt", which is 25 KB (as measured in Microsoft Windows®) and was created on Jun. 12, 2019, is filed herewith by electronic submission and is incorporated by reference herein.

BACKGROUND OF THE INVENTION

1. Field of the Invention

The present invention relates generally to the field of cancer biology. More particularly, it concerns HER3 targeting monoclonal antibodies for the treatment and detection of cancer.

2. Description of Related Art

The epidermal growth factor receptor (EGFR) family (ErbB/HER) consists of four known members: EGFR (HER1, erbB-1), HER2 (erbB-2), HER3 (erbB-3), and HER4 (erbB-4). Each receptor protein has the same basic structure, consisting of an extracellular amino-terminal domain, a single transmembrane spanning sequence and an intracellular cytoplasmic domain. ErbB signaling has a complex network with more than 11 interacting ligands for distinct binding specificities and activation of signaling pathways. The complex contents and interactions of HER receptors and ligands provide a great potential for significant signal diversification.

Growing evidence indicates that HER3 plays important role in the resistance mechanisms of HER targeting therapeutics including both small molecule tyrosine kinase inhibitors (TKIs), such as gefitinib, erlotinib and lapatinib, and HER family receptor targeting monoclonal antibodies, such as trastuzumab, cetuximab, panitumumab and pertuzumab. Heregulin/Neuregulin (NRG) is a member of a complex ligand family interacting with HER3 and HER4. Neuregulin binding activates ErbB3 and leads to formation of heterodimeric receptor complexes and activation of down stream signaling of HER3 through both PI3K/AKT and Ras/Raf/MAPK pathways. Therefore, HER3-binding monoclonal antibodies to block neuregulin binding have the potential to block HER3 signaling and inhibit cancer cell proliferation.

SUMMARY OF THE INVENTION

Described herein are HER3 monoclonal antibodies that potently block HER3 signaling and inhibit cancer cell proliferation. Thus, in a first embodiment, there is provided an isolated or recombinant monoclonal antibody that specifically binds to a HER3. In certain aspects, an antibody competes for the binding of a HER3 with the Rab46, Rab1210, Rab189, or Rab774 monoclonal antibody. In certain aspects, the antibody may comprise all or part of the heavy chain variable region and/or light chain variable region of the Rab46, Rab1210, Rab189, or Rab774 monoclonal antibodies. In a further aspect, the antibody may comprise an amino acid sequence that corresponds to a first, second, and/or third complementarity determining region (CDR) from the light variable and/or heavy variable chain of the Rab46, Rab1210, Rab189, or Rab774 monoclonal antibodies of the present embodiments.

In certain aspects, the isolated antibody comprises CDR sequences at least 80%, 90%, or 95% identical to the CDR regions of the Rab46, Rab1210, Rab189, or Rab774 heavye and light chain amino acid sequences. In further aspects, an antibody comprises CDR regions identical to the Rab46, Rab1210, Rab189, or Rab774 CDR regions, except for one or two amino acid substitutions, deletions, or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a Rab46, Rab1210, Rab189, or Rab774 monoclonal antibody. Thus, in some specific aspects, an antibody of the embodiments comprises (a) a first $V_H$ CDR at least 80% identical to $V_H$ CDR1 of Rab46 (SEQ ID NO: 9), Rab1210 (SEQ ID NO: 15), Rab189 (SEQ ID NO: 21), or Rab774 (SEQ ID NO: 27); (b) a second $V_H$ CDR at least 80% identical to $V_H$ CDR2 of Rab46 (SEQ ID NO: 10), Rab1210 (SEQ ID NO: 16), Rab189 (SEQ ID NO: 22), or Rab774 (SEQ ID NO: 28); (c) a third $V_H$ CDR at least 80% identical to $V_H$ CDR3 of Rab46 (SEQ ID NO: 11), Rab1210 (SEQ ID NO: 17), Rab189 (SEQ ID NO: 23), or Rab774 (SEQ ID NO: 29); (d) a first $V_L$ CDR at least 80% identical to $V_L$ CDR1 of Rab46 (SEQ ID NO: 12), Rab1210 (SEQ ID NO: 18), Rab189 (SEQ ID NO: 24), or Rab774 (SEQ ID NO: 30); (e) a second $V_L$ CDR at least 80% identical to $V_L$ CDR2 of Rab46 (SEQ ID NO: 13), Rab1210 (SEQ ID NO: 19), Rab189 (SEQ ID NO: 25), or Rab774 (SEQ ID NO: 31); and (f) a third $V_L$ CDR at least 80% identical to $V_L$ CDR3 of Rab46 (SEQ ID NO: 14), Rab1210 (SEQ ID NO: 20), Rab189 (SEQ ID NO: 26), or Rab774 (SEQ ID NO: 32). In certain aspects, such an antibody is a humanized or de-immunized antibody comprising the foregoing CDRs on a human IgGs (e.g., IgG1, IgG2, IgG4, or a genetically modified IgG) backbone.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Rab46, which are represented by SEQ ID NOs: 9, 10, 11, 12, 13, and 14, respectively. In one aspect, the isolated antibody comprises CDR sequences that are identical to the CDR sequences of monoclonal antibody Rab46.

In another aspect, the isolated antibody comprises a $V_H$ domain at least about 80% identical to the $V_H$ domain of Rab46 (SEQ ID NO: 1); hRab46H-1 (SEQ ID NO: 33); or hRab46H-2 (SEQ ID NO: 34); and a $V_L$ domain at least about 80% identical to the $V_L$ domain of Rab46 (SEQ ID NO: 2); hRab46L-1 (SEQ ID NO: 35); or hRab46L-2 (SEQ ID NO: 36). For example, the antibody can comprise a $V_H$ domain at least 95% identical to the $V_H$ domain of hRab46H-1 (SEQ ID NO: 33) and a $V_L$ domain at least 95% identical to the $V_L$ domain of hRab46L-1 (SEQ ID NO: 35) or hRab46L-2 (SEQ ID NO: 36). Thus, in some aspects, an antibody comprises a $V_H$ domain identical to the $V_H$ domain of hRab46H-1 (SEQ ID NO: 33) and a $V_L$ domain identical to the $V_L$ domain of hRab46L-1 (SEQ ID NO: 35). In further aspects an antibody comprises a $V_H$ domain identical to the $V_H$ domain of hRab46H-1 (SEQ ID NO: 33) and a $V_L$ domain identical to the $V_L$ domain hRab46L-2 (SEQ ID NO: 36). In another aspects an antibody comprises a $V_H$ domain at least 95% identical to the $V_H$ domain of hRab46H-2 (SEQ ID NO: 34) and a $V_L$ domain at least 95% identical to the $V_L$ domain of hRab46L-2 (SEQ ID NO: 36) or hRab46L-1 (SEQ ID NO: 35). For instance the antibody can comprise a $V_H$ domain identical to the $V_H$ domain of hRab46H-2 (SEQ ID NO: 34) and a $V_L$ domain identical to the $V_L$ domain of hRab46L-2 (SEQ ID NO: 36) or a $V_H$ domain identical to the $V_H$ domain of hRab46H-2 (SEQ ID NO: 34) and a $V_L$ domain identical to the $V_L$ domain of hRab46L-1 (SEQ ID NO: 35). In a specific example, the isolated antibody can comprise $V_H$ and $V_L$ domains identical to those of monoclonal antibody Rab46, HER3-hMab-A9, HER3-hMab-A10, HER3-hMab-A11, or HER3-hMab-A12. In still further aspects, the antibody is the HER3-hMab-A9, HER3-hMab-A10, HER3-hMab-A11, or HER3-hMab-A12 antibody.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Rab1210, which are represented by SEQ ID NOs: 15, 16, 17, 18, 19, and 20, respectively. In one aspect, the isolated antibody comprises CDR sequences that are identical to the CDR sequences of monoclonal antibody Rab1210.

In another aspect, the isolated antibody comprises a $V_H$ domain at least about 80% identical to the $V_H$ domain of Rab1210 (SEQ ID NO: 3); hRab1210H-1 (SEQ ID NO: 37); or hRab1210H-2 (SEQ ID NO: 38); and a $V_L$ domain at least about 80% identical to the $V_L$ domain of Rab1210 (SEQ ID NO: 4); hRab1210L-1 (SEQ ID NO: 39); or hRab1210L-2 (SEQ ID NO: 40). Thus, in some aspects, the antibody comprises a $V_H$ domain at least 95% identical to the $V_H$ domain of hRab1210H-1 (SEQ ID NO: 37) and a $V_L$ domain at least 95% identical to the $V_L$ domain of hRab1210L-1 (SEQ ID NO: 39) or hRab1210L-2 (SEQ ID NO: 40). For instance the antibody can comprise a $V_H$ domain identical to the $V_H$ domain of hRab1210H-1 (SEQ ID NO: 37) and a $V_L$ domain identical to the $V_L$ domain of hRab1210L-1 (SEQ ID NO: 39) or a $V_H$ domain identical to the $V_H$ domain of hRab1210H-1 (SEQ ID NO: 37) and a $V_L$ domain identical to the $V_L$ domain of hRab1210L-2 (SEQ ID NO: 40). In further aspects, an antibody comprises a $V_H$ domain at least 95% identical to the $V_H$ domain of hRab1210H-2 (SEQ ID NO: 38) and a $V_L$ domain at least 95% identical to the $V_L$ domain of hRab1210L-2 (SEQ ID NO: 40) or hRab1210L-1 (SEQ ID NO: 39). For example, the antibody can comprise a $V_H$ domain identical to the $V_H$ domain of hRab1210H-2 (SEQ ID NO: 38) and a $V_L$ domain identical to the $V_L$ domain of hRab1210L-2 (SEQ ID NO: 40) or a $V_H$ domain identical to the $V_H$ domain of hRab1210H-2 (SEQ ID NO: 38) and a $V_L$ domain identical to the $V_L$ domain of hRab1210L-1 (SEQ ID NO: 39). In a specific example, the isolated antibody can comprise $V_H$ and $V_L$ domains identical to those of monoclonal antibody Rab1210, HER3-hMab-A13, HER3-hMab-A14, HER3-hMab-A15 or HER3-hMab-A16. In still further aspects, the antibody is the HER3-hMab-A13, HER3-hMab-A14, HER3-hMab-A15 or HER3-hMab-A16 antibody.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Rab189, which are represented by SEQ ID NOs: 21, 22, 23, 24, 25, and 26, respectively. In one aspect, the isolated antibody comprises CDR sequences that are identical to the CDR sequences of monoclonal antibody Rab189.

In another aspect, the isolated antibody comprises a $V_H$ domain at least about 80% identical to the $V_H$ domain of Rab189 (SEQ ID NO: 5) and a $V_L$ domain at least about 80% identical to the $V_L$ domain of Rab189 (SEQ ID NO: 6). In one aspect, the isolated antibody comprises $V_H$ and $V_L$ domains identical to those of monoclonal antibody Rab189.

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody Rab774, which are represented by SEQ ID NOs: 27, 28, 29, 30, 31, and 32, respectively. In one aspect, the isolated antibody comprises CDR sequences that are identical to the CDR sequences of monoclonal antibody Rab774.

In another aspect, the isolated antibody comprises a $V_H$ domain at least about 80% identical to the $V_H$ domain of Rab774 (SEQ ID NO: 7) and a $V_L$ domain at least about 80% identical to the $V_L$ domain of Rab774 (SEQ ID NO: 8). In one aspect, the isolated antibody comprises $V_H$ and $V_L$ domains identical to those of monoclonal antibody Rab774.

In some aspects, an antibody of the embodiments may be an IgG (e.g., IgG1, IgG2, IgG3 or IgG4), IgM, IgA, genetically modified IgG isotype, or an antigen binding fragment thereof. The antibody may be a Fab', a F(ab')2 a F(ab')3, a monovalent scFv, a bivalent scFv, a bispecific or a single domain antibody. The antibody may be a human, humanized, or de-immunized antibody. In a further aspect, the isolated antibody is the Rab46, Rab1210, Rab189, or Rab774 antibody.

In some aspects, the antibody may be conjugated to an imaging agent, a chemotherapeutic agent, a toxin, or a radionuclide.

In one embodiment, there is provided a recombinant polypeptide comprising an antibody $V_H$ domain comprising CDRs 1-3 of the $V_H$ domain of Rab46 (SEQ ID NOs: 9, 10, and 11); CDRs 1-3 of the $V_H$ domain of Rab1210 (SEQ ID NOs: 15, 16, and 17); CDRs 1-3 of the $V_H$ domain of Rab189 (SEQ ID NOs: 21, 22, and 23); or CDRs 1-3 of the $V_H$ domain of Rab774 (SEQ ID NOs: 27, 28, and 29). In another embodiment, there is provided a recombinant polypeptide comprising an antibody $V_L$ domain comprising CDRs 1-3 of the $V_L$ domain of Rab46 (SEQ ID NOs: 12, 13, and 14); Rab1210 (SEQ ID NOs: 18, 19, and 20); Rab189 (SEQ ID NOs: 24, 25, and 26); or Rab774 (SEQ ID NOs: 30, 31, and 32).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering an effective amount of an antibody disclosed herein. In certain aspects, the antibody is a monoclonal antibody of the present invention, such as the Rab46, Rab1210, Rab189, Rab774, HER3-hMab-A9, HER3-hMab-A10, HER3-hMab-A11, HER3-hMab-A12, HER3-hMab-A13, HER3-hMab-A14, HER3-hMab-A15 or HER3-hMab-A16 antibody or a recombinant polypeptide comprising antibody segment derived therefrom.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In another embodiment, there is provided a method for detecting a cancer in a subject comprising testing for the presence of elevated HER3 relative to a control in a sample from the subject, wherein the testing comprises contacting the sample with an antibody disclosed herein. For example, the method may be an in vitro or in vivo method.

Certain embodiments are directed to an antibody or recombinant polypeptide composition comprising an isolated and/or recombinant antibody or polypeptide that specifically binds HER3. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a HER3-binding antibody as provided in Table 6 or Chart 1.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a HER3-binding antibody as provided in Table 6 or Chart 1.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a HER3-binding antibody (as provided in Table 6 and Chart 1). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a HER3-binding antibody as provided in Table 6 and Chart 1.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. Antibodies of the Invention

In certain embodiments, an antibody or a fragment thereof that binds to at least a portion of HER3 protein and inhibits HER3 signaling and cancer cell proliferation are contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand.

Figure 8:
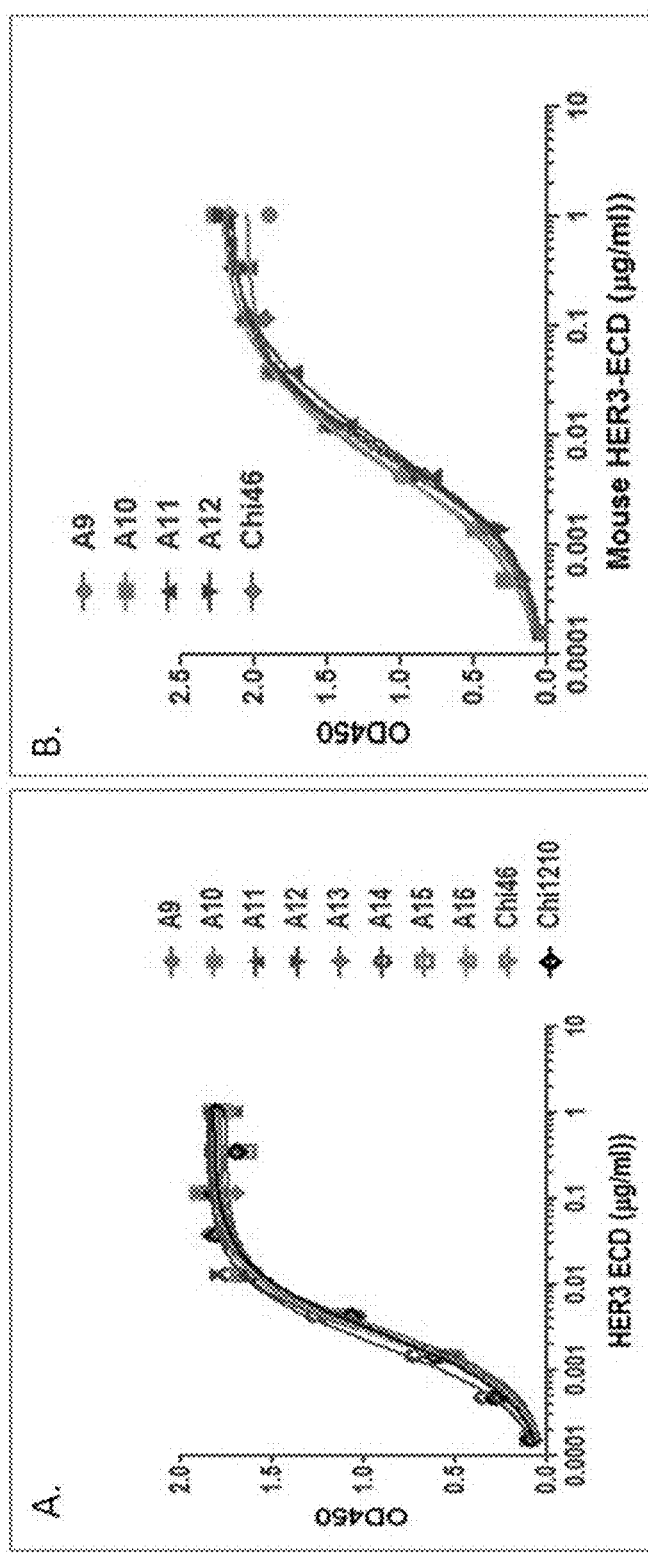
FIGS. 8A-B. Concentration dependent binding of the humanized HER3 monoclonal antibodies on HER3 ECD by ELISA.
Figure 9:
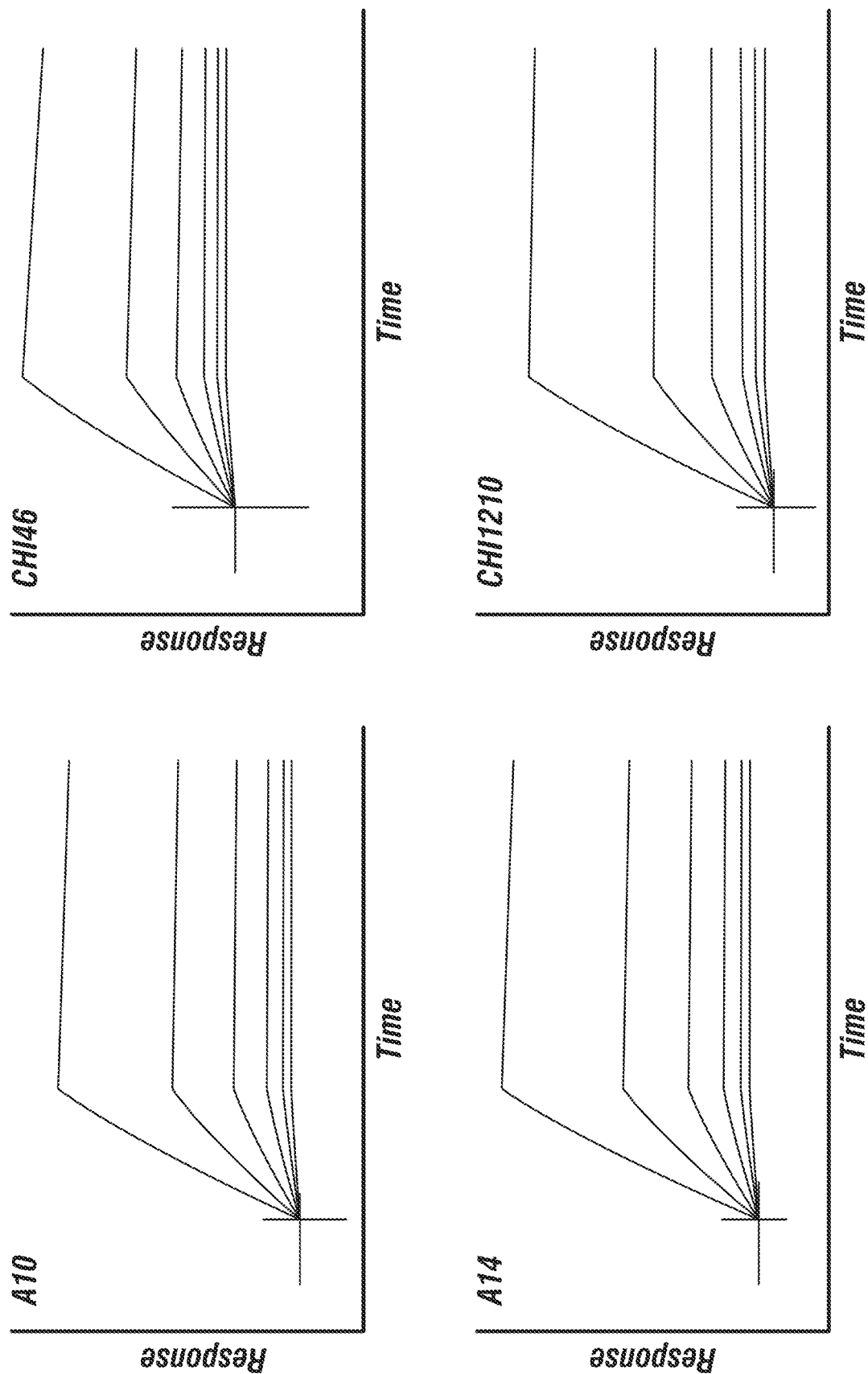
FIG. 9. Kinetic binding affinity of the humanized HER3 monoclonal antibodies on HER3 ECD by Biacore assay.
Figure 10:
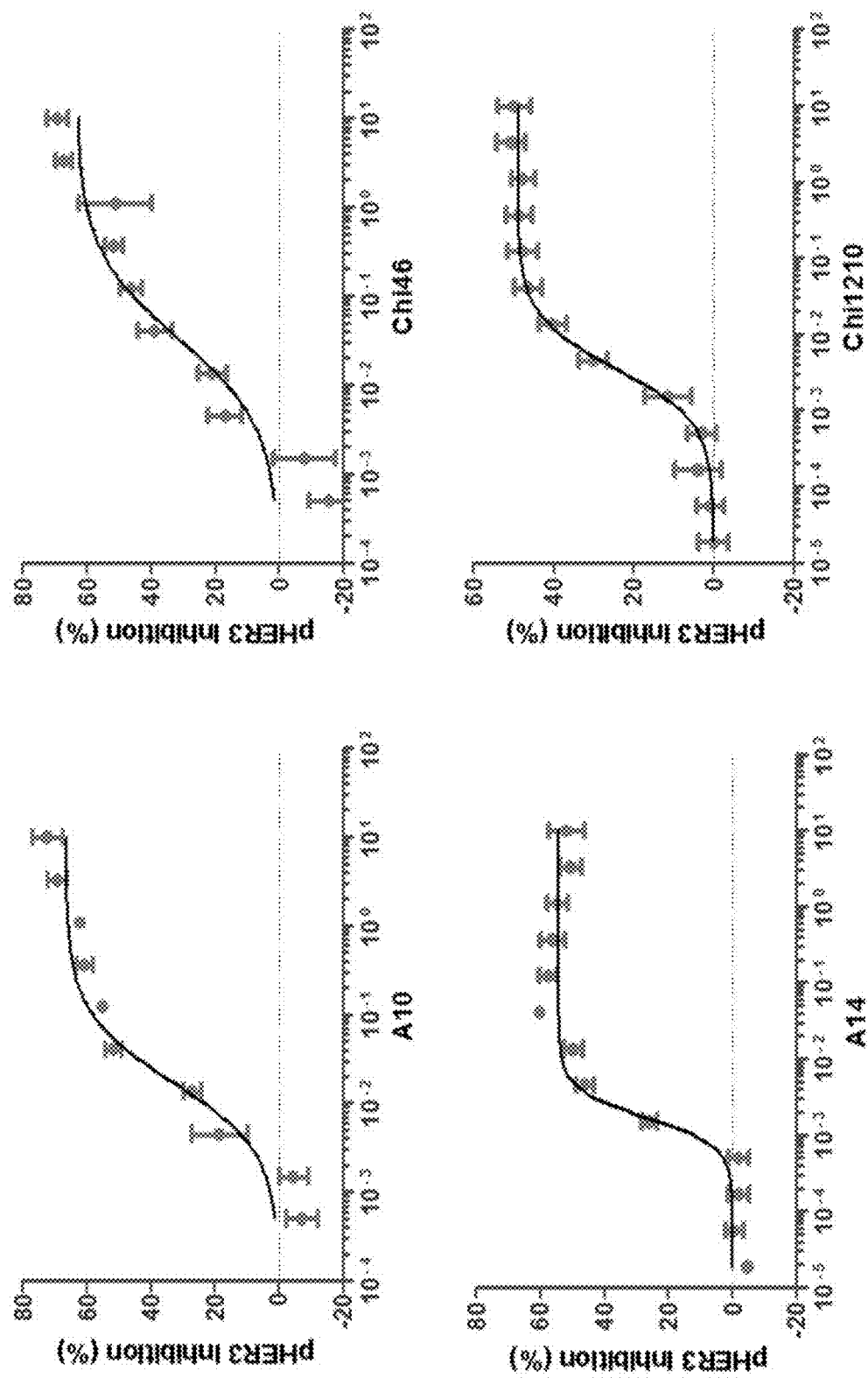
FIG. 10. Concentration dependent inhibition of pHER3 by the humanized HER3 monoclonal antibodies in T47D cancer cells.
Figure 11:
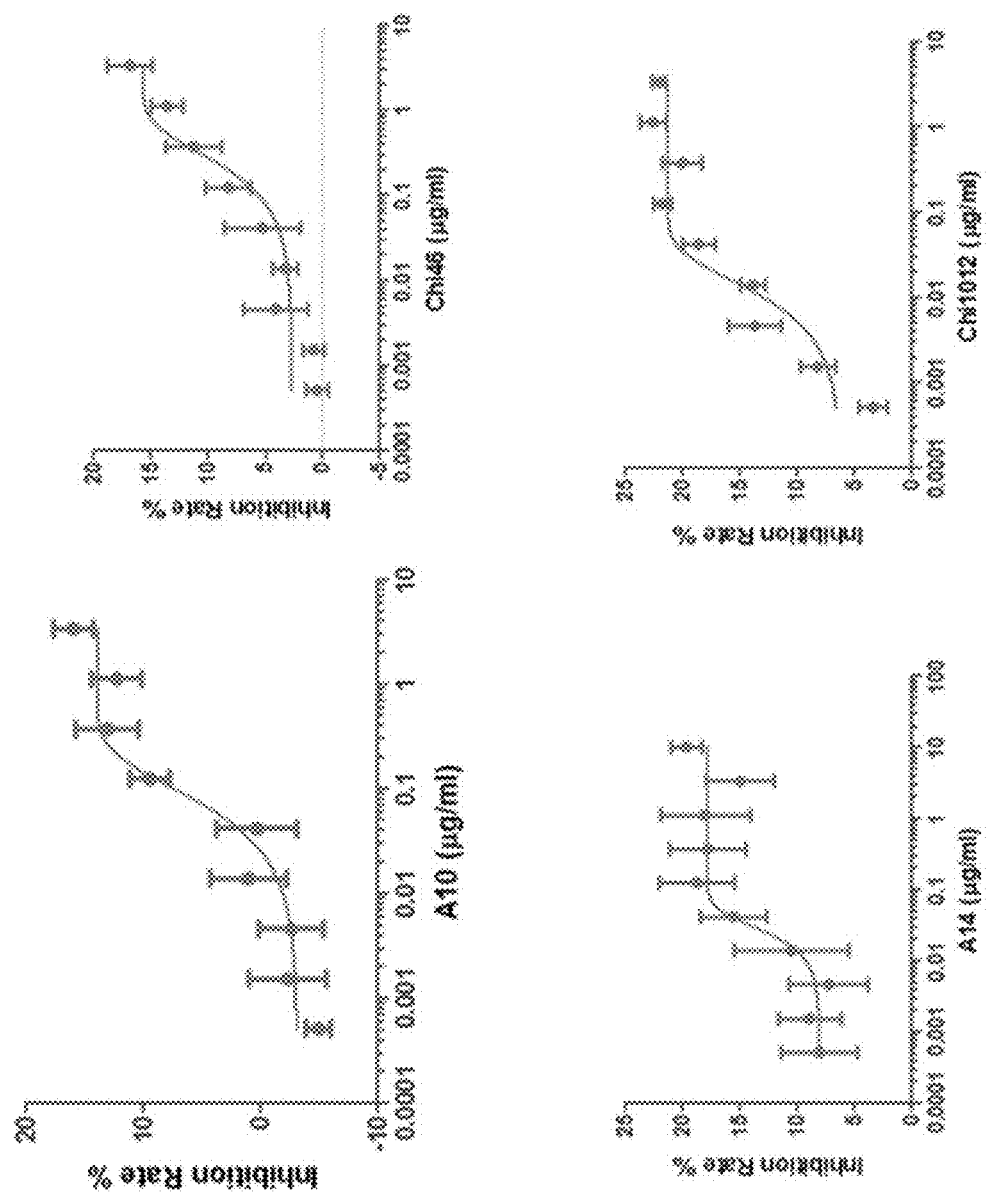
FIG. 11. Concentration dependent inhibition of CWR22 cancer cell proliferation by the humanized HER3 monoclonal antibodies.
Figure 12:
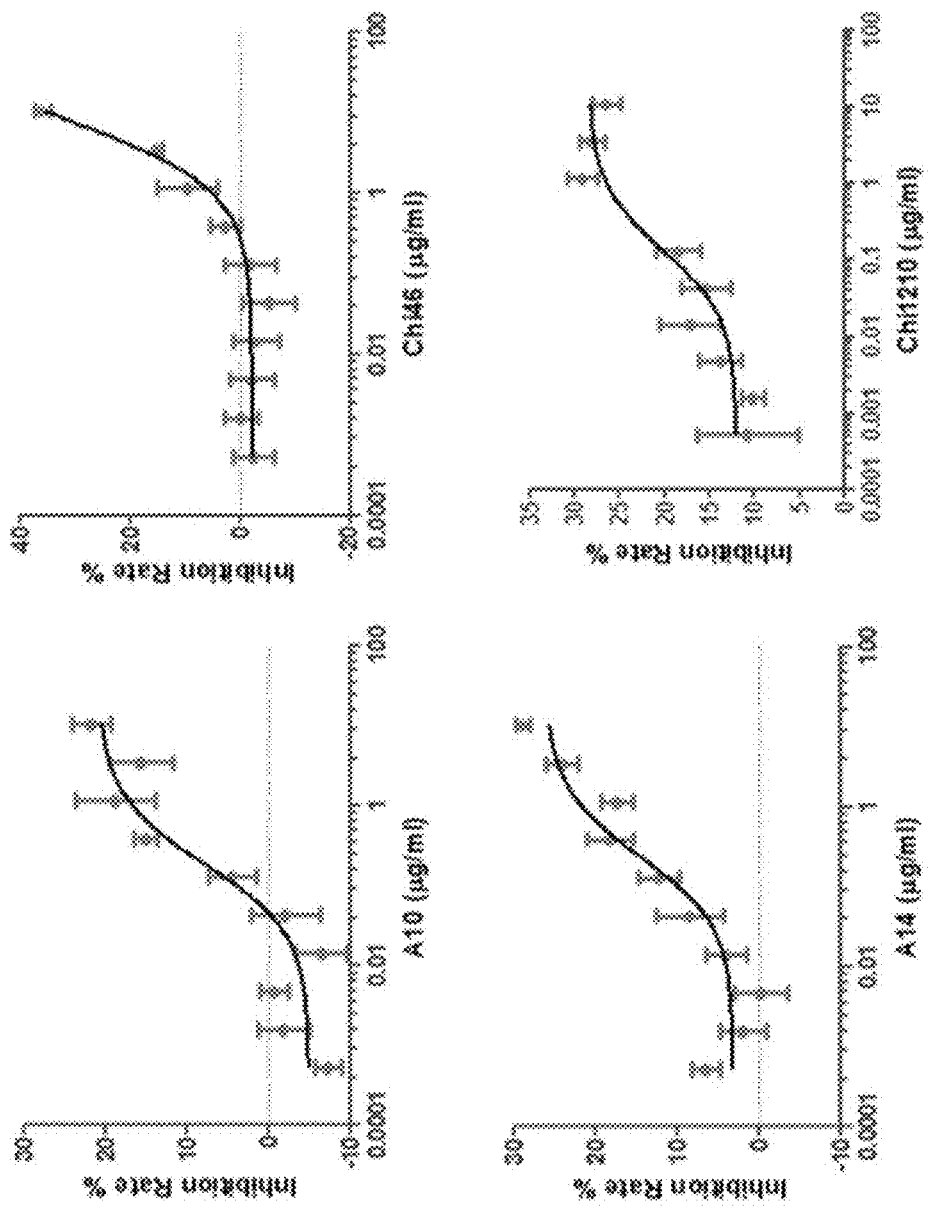
FIG. 12. Concentration dependent inhibition of MCF-7 cancer cell proliferation by the humanized HER3 monoclonal antibodies.

Preferably, the anti-HER3 antibody is a monoclonal antibody or a humanized antibody. Indeed studies presented herein demonstrated that the identified CDRs for HER3-binding antibodies could be placed in a human frame work and the resulting humanized antibodies retained high affinity for HER3 (FIG. 8-9). Importantly the humanized antibodies also efficiently inhibited HER3 signaling (FIG. 10) and were able to inhibit cancer cell replication in a HER3 positive cancer cells (FIGS. 11-12). Thus, the HER3-binding antibodies provided herein, in particular the humanized antibodies, are promising candidates for new anticancer therapeutics.

Thus, by known means and as described herein, polyclonal or monoclonal antibodies, antibody fragments, and binding domains and CDRs (including engineered forms of any of the foregoing) may be created that are specific to HER3 protein, one or more of its respective epitopes, or conjugates of any of the foregoing, whether such antigens or epitopes are isolated from natural sources or are synthetic derivatives or variants of the natural compounds. Another variation is the construction of bispecific antibodies in which one heavy chain targeting HER3 and other heavy chain targeting a different cancer target, such as HER2, EGFR, IGF1R, cMet, or other cell surface targets.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a HER3 extracellular domain protein (amino acids 1-643 of NCBI Accession No. M34309), in order to produce antibodies specific for HER3 protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a HER3 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells may be isolated from freshly prepared rabbit peripheral blood mononuclear cells of immunized rabbits and further selected for HER3 binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into E. coli. HER3 specific binding Fab may be selected out through multiple rounds enrichment panning and sequenced. Selected HER3 binding hits may be expressed as full length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to HER3 will have the ability to neutralize or counteract the effects of HER3 regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds HER3.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against HER3, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabel s, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6?-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. Treatment of Diseases

Certain aspects of the present embodiments can be used to prevent or treat a disease or disorder associated with HER3 signaling. Signaling of HER3 may be reduced by any suitable drugs to prevent cancer cell proliferation. Preferably, such substances would be an anti-HER3 antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the HER3 signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an inhibitory antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve an antibody or an antibody fragment against HER3 to inhibit its activity in cancer cell proliferation, in combination with a second or additional therapy. Such therapy can be applied in the treatment of any disease that is associated with HER3-mediated cell proliferation. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

i. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and angui dine); urethan; vindesine; dacarb azine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine;

vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

ii. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

iii. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., Mycobacterium bovis, Plasmodium falciparum, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

iv. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies.Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, at least one HER3 antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1:
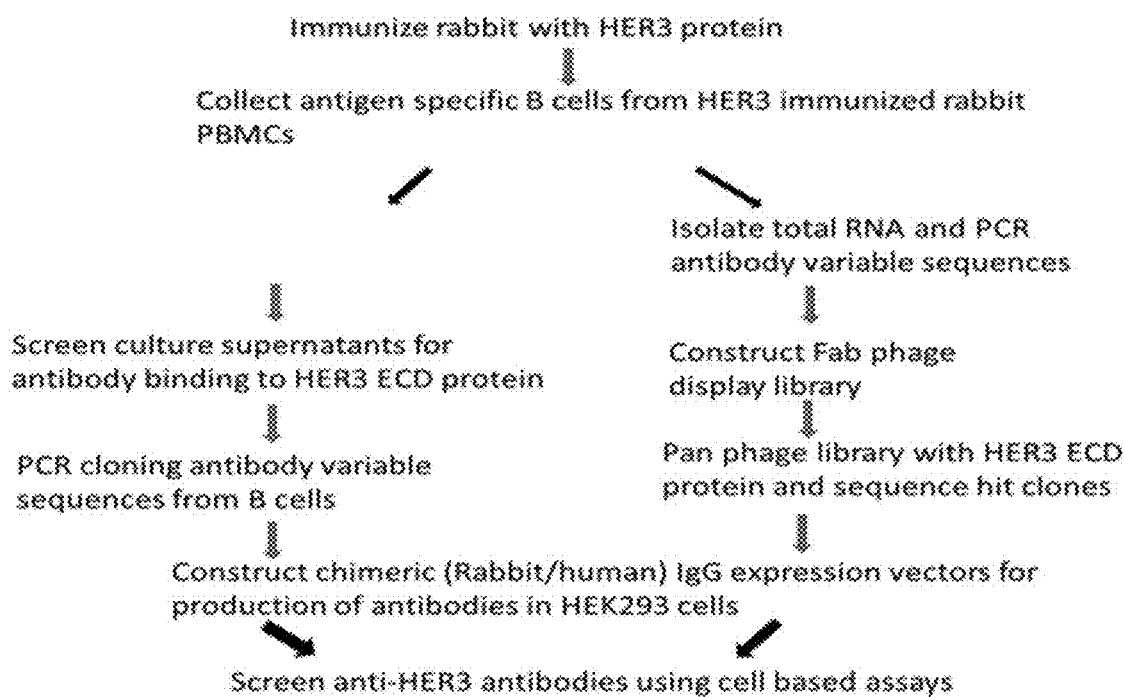
FIG. 1. Process flow for antibody selection.
Figure 2:
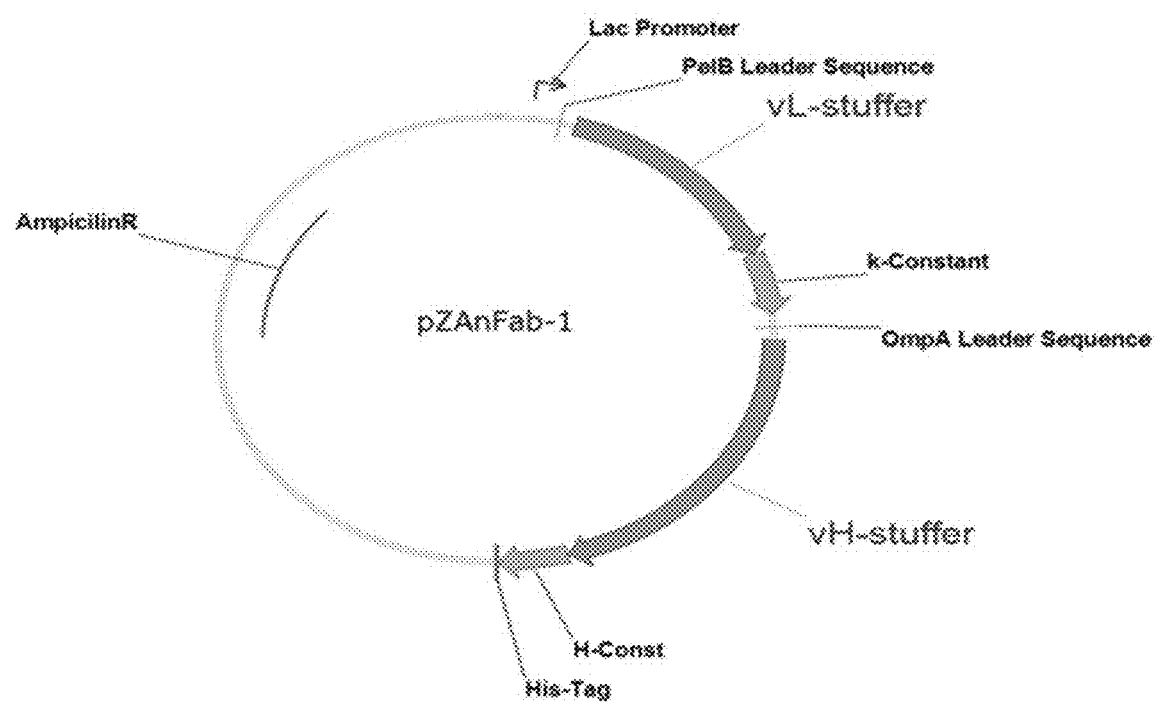
FIG. 2. Phage display vector for Rabbit Fab expression.

Generation of Rabbit Monoclonal Antibodies from a Phage Display Fab Library Using HER3 Antigen Binding Plasma B Cells Isolated from Antigen Immunized Rabbit ErbB3 (Genebank accession no. M34309) extracellular domain (ECD) (amino acids Met1-Thr643) protein was used to immunize New Zealand rabbits at Bethyl laboratories, Inc (Montgomery, Tex.). Rabbits were immunized with 100 µg per rabbit dosing. After initial immunization, two boost dosings were administered with a 2-3 week interval between dosings. The titer of anti-Her3 sera was determined by a series of dilutions of serum in ELISA by coating HER3 ECD protein on 96-well plates (max-sorb plates, Nunc) and binding antibodies were detected with an anti-rabbit antibody conjugated with horseradish peroxidase (HRP) and TMB substrate. Absorbance at 450 nm was used to determine the antibody serum titer. When the titer reached $>10^6$, whole blood samples were withdrawn from the immunized rabbits and plasma B cells (CD45+CD5-CD19+) were isolated from the freshly prepared rabbit peripheral blood mononuclear cells using a fluorescence assisted cell sorting (FACS) instrument (BD FACSAria™ III, BD Biosciences). The isolated plasma cells were further selected for HER3 binding cells. After enrichment of antibody producing B cells, total RNA was isolated and cDNA was synthesized using a superscript reverse transcriptase II (Invitrogen) according to manufacturer's suggestion. DNA sequences of antibody variable regions from both heavy chains and light chains were amplified by polymerase chain reaction (PCR) using a set of designed primers (Table 1), see, e.g., Ridder et al., 2001, incorporated herein by reference. The amplified DNA was constructed into a phage display Fab expression vector (FIG. 2) and transformed into *E. coli* (TG1) cells. A library size of $10^{8-9}$ was constructed in the phage display vector system and HER3 specific binding Fab was selected out through two rounds enrichment panning and sequenced (Lone Star Labs, Tex.). The process flow for antibody selection is illustrated in FIG. 1.

Selected HER3 binding hits were expressed as full length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit. Purified HER3 antibodies were characterized for various biological properties.

TABLE 1

PCR primer sets for cloning variable heavy and light chain cDNA sequences from rabbit plasma B cells

| Primer name | Sequence |
| --- | --- |
| RVκF1 | CGGCCTCTAGAGAGCTCGTGMTGACCCAGACT (SEQ ID NO: 41) |
| RVκF2 | CGGCCTCTAGAGAGCTCGATMTGACCCAGACT (SEQ ID NO: 42) |
| RVκR1 | GCATCCGTACGTCGTAGGATCTCCAGCTCGGT (SEQ ID NO: 43) |
| RVκR2 | GCATCCGTACGTCGTTTGATTTCCACATTGGT (SEQ ID NO: 44) |
| RVκR3 | GCATCCGTACGTCGTTTGACSACCACCTCGGT (SEQ ID NO: 45) |
| RVλ F | ACAAGTCTAGAGAGCTCGTGCTGACTCAGTC (SEQ ID NO: 46) |
| RVλ R | CATCCGTACGTCGGCCTGTGACGGTCAGCT (SEQ ID NO: 47) |
| RVH F1 | CTTCCCTCGAGCAGTCGGTGGAGGAGTCCRGG (SEQ ID NO: 48) |
| RVH F2 | CTTCCCTCGAGCAGTCGGTGAAGGAGTCCGAG (SEQ ID NO: 49) |
| RVH F3 | CTTCCCTCGAGCAGTCGYTGGAGGAGTCCGGG (SEQ ID NO: 50) |
| RVH F4 | CTTCCCTCGAGCAGSAGCAGCTGRTGGAGTCC (SEQ ID NO: 51) |
| RVH R1 | CATCGGGCCCTTGGTGGAGGCTGARGAGAYGGTGACCAGG (SEQ ID NO: 52) |

Example 2

Figure 3:
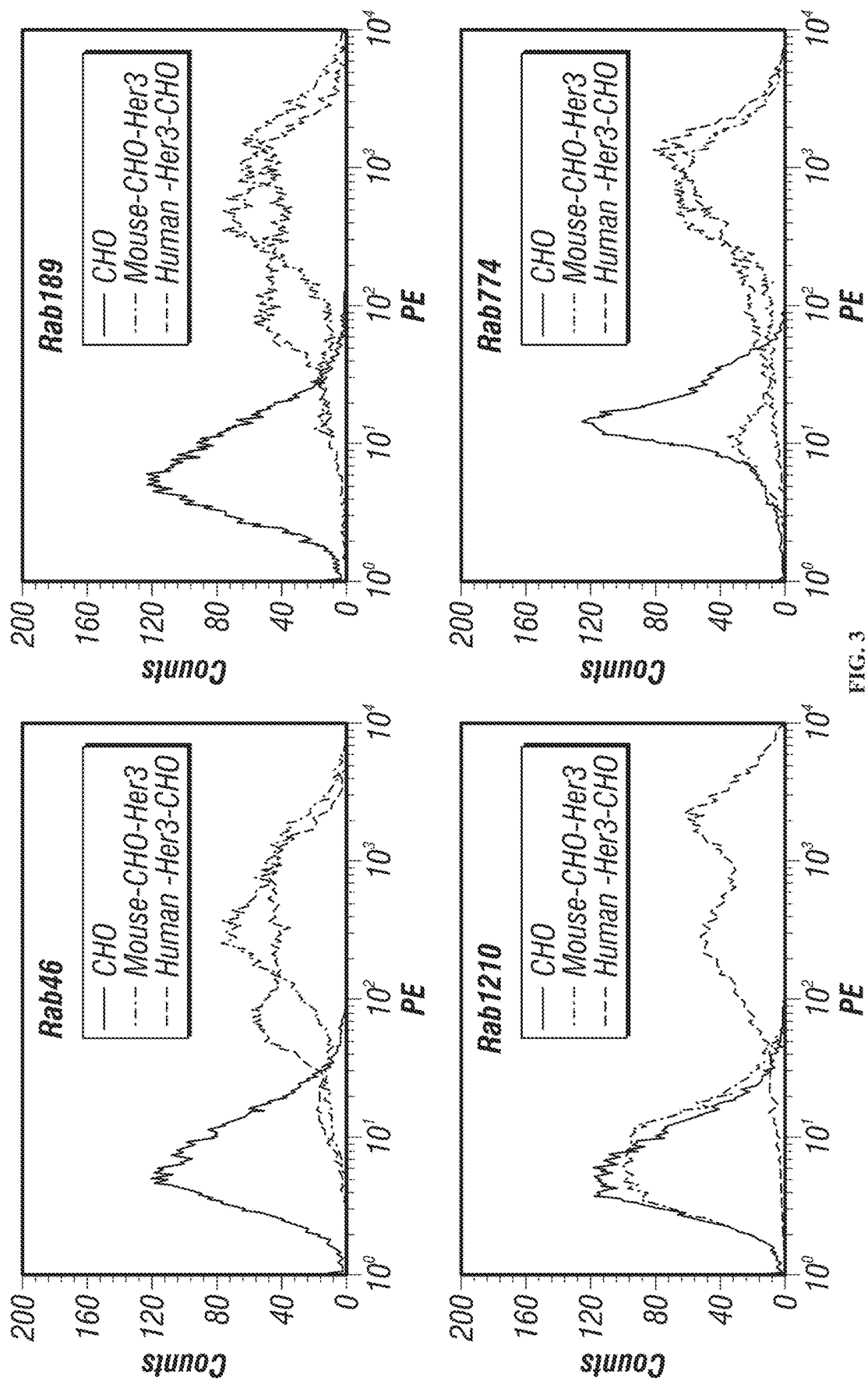
FIG. 3. Binding of anti-Her3 antibodies on human and mouse HER3/ErbB3 using heterologous HER3 expressing CHO cells.

Measurements of Binding of Human and Mouse HER3/ErbB3 with Flow Cytometry and ELISA CHO Flp-in (Invitrogen) cell lines expressing human or mouse HER3 receptors were used to study binding of the HER3 antibodies on cell surface receptors. HER3 expressing cells were detached using enzyme free-EDTA dissociation solution and resuspended in PBS, 2% FBS at a concentration of approximately $1 \times 10^6$ cells/ml. The cells were stained with the purified HER3 IgGs at 4° C. for 40 minutes and washed twice in PBS with 2% FBS by centrifugation at 1200 rpm for 10 minutes. Supernatant was removed and cells were stained with R-PE conjugated anti-rabbit IgG at 4° C. for 30 min. Then cells were washed with 4 mL PBS with 2% FBS and were analyzed on a flow cytometer (Quava, Millipore). FIG. 3 shows the binding of the rabbit HER3 antibody on human and mouse HER3 expression cells as indicated by the increase of fluorescence intensity (X-axis) in comparison with non-specific rabbit IgG binding control.

Example 3

Determination of HER3 Binding Affinity Using Surface Plasmon Resonance (SPR) Assay with Biacore T-100

All experiments were performed at 25° C. at a flow rate of 45 μl/min. To prepare a BIAcore assay, an anti-rabbit IgG antibody (50 μg/ml each in acetate buffer, pH 5.0) was immobilized onto a carboxymethyl dextran sensorchip (CM5) using amine coupling procedures as described by the manufacturer. Purified rabbit Mabs to be tested were diluted at a concentration of 5 μg/ml in 0.5% P20, HBS-EP buffer and injected on FC2 to reach 500 to 1000 RU. FC1 was used as the reference cell. Specific signals correspond to the difference of signals obtained on FC2 versus FC1. The analyte (recombinant human HER3, apparent molecular weight 97 kDa on SDS-PAGE gel) was injected during 90 sec at series of concentration dilutions (100, 50, 25, 12.5, 6.25, and 3.13, 1.56 nM) in 0.5% P20, HBS-EP buffer. These concentrations were prepared from stock solution in 0.5% P20, HBS-EP. The dissociation phase of the analyte was monitored over a 30 minute period. Running buffer was also injected under the same conditions as a double reference. After each running cycle, both flow cells were regenerated by injecting 20 to 45 μl of glycine-HCl buffer pH 1.5. Binding $K_D$ on HER3 was calculated by koff/kon kinetic rate for each HER3 monoclonal antibody (Table 2).

TABLE 2

HER3 antibody binding kinetic constants on human HER3/ErbB3 extracellular domain determined using BIAcore (SPR) analysis

| Purified monoclonal HER3 antibody | $K_D$ (nM) |
| --- | --- |
| Rab46 | 7.3 ± 0.13 |
| Rab1210 | 1.0 ± 0.05 |
| Rab189 | 3.6 ± 0.16 |
| Rab774 | 0.16 ± 0.01 |

Example 4

Internalization Study of HER3 Monoclonal Antibodies

T47D breast cancer cells were cultured to 80% confluency. The cells were detached and resuspended in complete culture medium for accounting cells. Cells at a concentration of approximately $1 \times 10^7$/ml were incubated at 37° C. for 3 hr in the presence and absence of HER3 IgG at 2 μg/ml. Then cells were washed with 4 mL PBS, 2% FBS and stained with the HER3 antibody (10 μg/ml) as primary binding antibody at 4° C. for 40 minutes. After washing with PBS, 2% FBS, cells were stained with 0.5 μg R-PE conjugated goat anti-rabbit antibody (BD Pharmingen) at 4° C. for 30 minutes, covered with foil. Cells were washed with 4 mL PBS, 2% FBS, then centrifuged at 1200 rpm for 10 minutes. Cells were fixed in PBS/10% formaldehyde and analyzed using a flow cytometer (Quava, Millipore). Percentage of HER3 receptor internalization mediated by the isolated HER3 monoclonal antibodies was calculated by the formula: (mean fluorescence intensity (MFI) of no antibody control-MFI of antibody treated cells)/MFI of controls×100, shown in Table 3.

TABLE 3

Percentage of HER3 receptor internalization mediated by anti-HER3 antibodies

| HER3 monoclonal antibody | % Receptor Internalization |
| --- | --- |
| Rab46 | 39 ± 5 |
| Rab1210 | 62 ± 5 |
| Rab189 | 55 ± 4 |
| Rab774 | 60 ± 8 |

Example 5

Inhibition of pHER3, pAKT, and pERK1/2 by Rabbit HER3 Monoclonal Antibodies

MCF7 cells were seeded at cell density approximately $3 \times 10^5$ cells/ml in 96-well plates and cultured over night. Cell culture media were changed to low serum (0.5% FBS) for 15 hours, cells were treated with the isolated HER3 monoclonal antibodies for 2 hr at 37° C. Cells were stimulated with 3.3 nM rhNRG1-β1 for 20 minutes at 37° C. before making cell lysates. Before making cell lysates, cells were washed with cold PBS, 0.5% BSA, for 3 times. Cell Extraction Buffer (containing fresh 1 mM PMSF, protease inhibitor cocktail, and phosphatase inhibitor cocktail) was added into each well for 30 min with gentle rocking at 4° C. After lysate was mixed by pipetting up-down for 3-5 times, the plate was centrifuged at 3,000 rpm for 10 min and cell supernatants were used in following assays.

Figure 4:
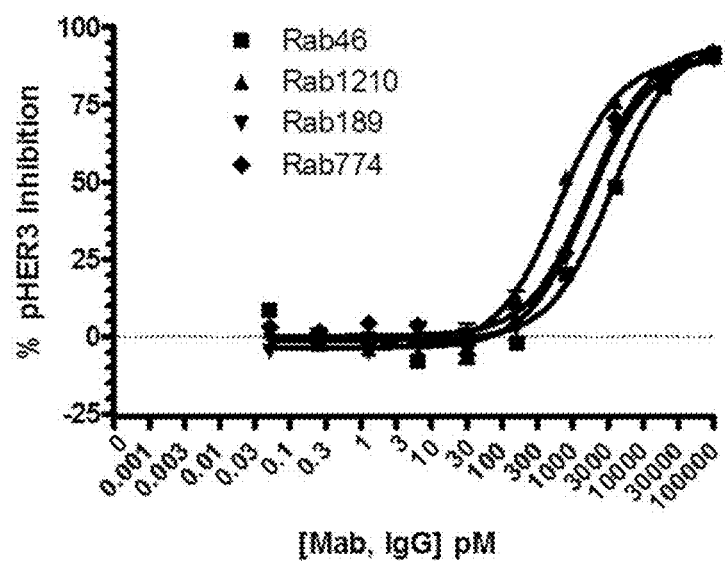
FIG. 4. Dose response of purified anti-Her3 IgGs in inhibition of HER3 phosphorylation assay.

For pHER3 inhibition assay, maxi-sorp plate (Costar 96 well plates) was coated with 4 μg/ml mouse anti-human HER3 antibody (R&D Systems) at 4° C. for over night and was blocked with PBS containing 2% BSA for 2 hours at room temperature. 100 μl of cell supernatant was transferred to the blocked assay plate and incubated for 2 hr at RT. Plates were washed with 300 μl PBS with Tween 20 (0.05%) for 5 times. Then secondary antibody, anti-p-tyrosine-HRP (R&D Systems), was added and incubated for 1 hr at RT before detection. Washing steps were repeated and HRP chemiluminescence substrate (Millipore, Calif.) was added for 5 minutes with gentle rocking at RT, then luminescent signals were read using a plate reader (Molecular Devices, CA). Percentage of inhibition of pHER3 was calculated using the formula: (signals of cells without antibody treatment-signals of antibody treated cells)/signals of controls×100. Average of 3-4 replications was used in the concentration dependent inhibition assay (FIG. 4). $IC_{50}$s determined using the titration curve fit by GraphPad prism (v5.1) are listed in the Table 4.

Figure 5:
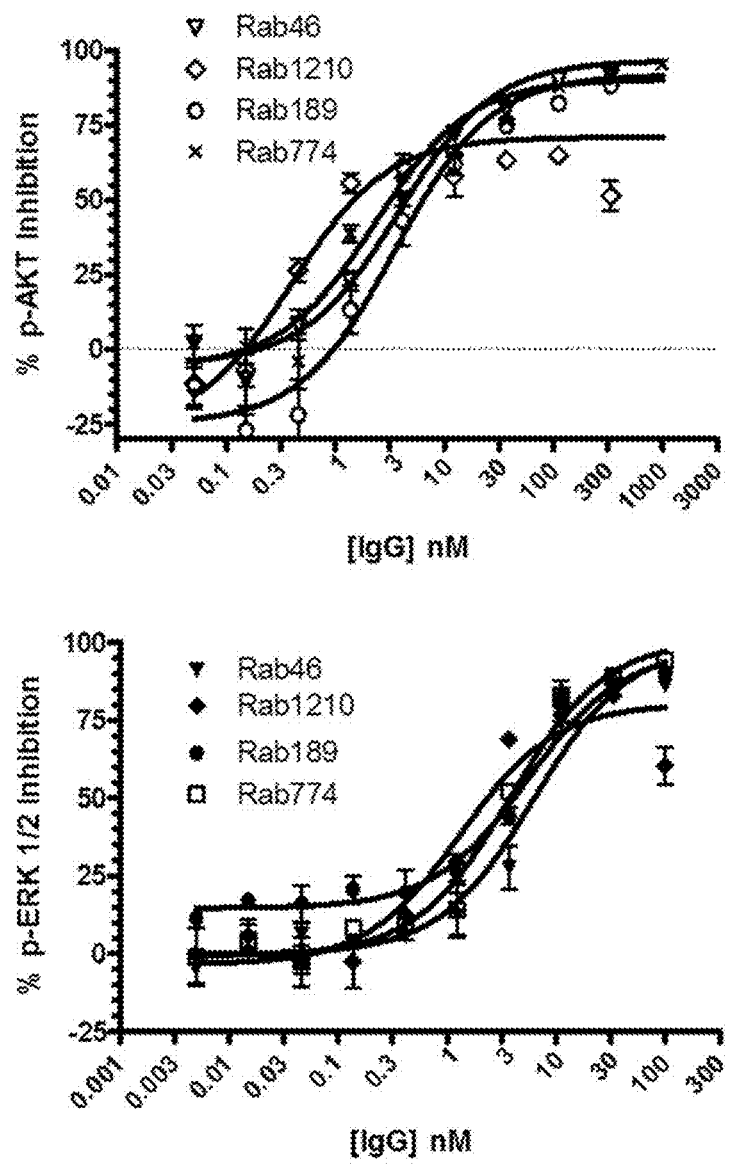
FIG. 5. pAKT and pERK inhibition by HER3 Mab IgGs in MCF7 cells.

For pAKT inhibition assay, similar ELISA format was used for capturing total AKT proteins using an antibody from R&D Systems. After washing the plates with 300 µl/well PBS-T for 5 times and secondary antibody, biotinylated rabbit anti-human phospho-Akt (S473) was added for 1 hr incubation at RT. Streptavidin-HRP was used for detection by incubation for 20 min at RT. After washing the plates, HRP chemiluminescence substrate was added for 5-10 minutes and plate was read using a plate reader (Molecular Devices). Percentage of inhibition of pAKT was calculated using the formula: (signals of cells without antibody treatment-signals of antibody treated cells)/signals of controls×100. Average of 3-4 replications was used in the concentration dependent inhibition assay (FIG. 5). $IC_5$ s determined using the titration curve fit by GraphPad prism (v5.1) are listed in the Table 4.

For pERK1/2 inhibition assay, Meso Scale Discovery (MSD) pre-coated plate was blocked with TRIS buffer containing 3% BSA with shaking. Cell lysates (25 µl/well) were transferred to the blocked assay plate and incubated for 2 hr at RT with shaking. Wells were washed with 300 µl/well Tris buffer for 3 times and detected with MSD anti-phospho-ERK1/2 (T/Y: 202/204; 185/187) antibody and SULFO-TAG™ solution from MSD assay kit according to the manufacturer's suggestion. Plate was read on MSD SECTOR™ Imager 2400 and data was analyzed using the formula: (signals of cells without antibody treatment-signals of antibody treated cells)/signals of controls×100. Average of 3-4 replications was used in the concentration dependent inhibition assay (FIG. 5). $IC_{50}$ determined using the titration curve fit by GraphPad prism (v5.1) are listed in the Table 4.

Example 6

Blocking Ligand Neuregulin Binding on HER3 by the HER3 Monoclonal Antibodies

Figure 6:
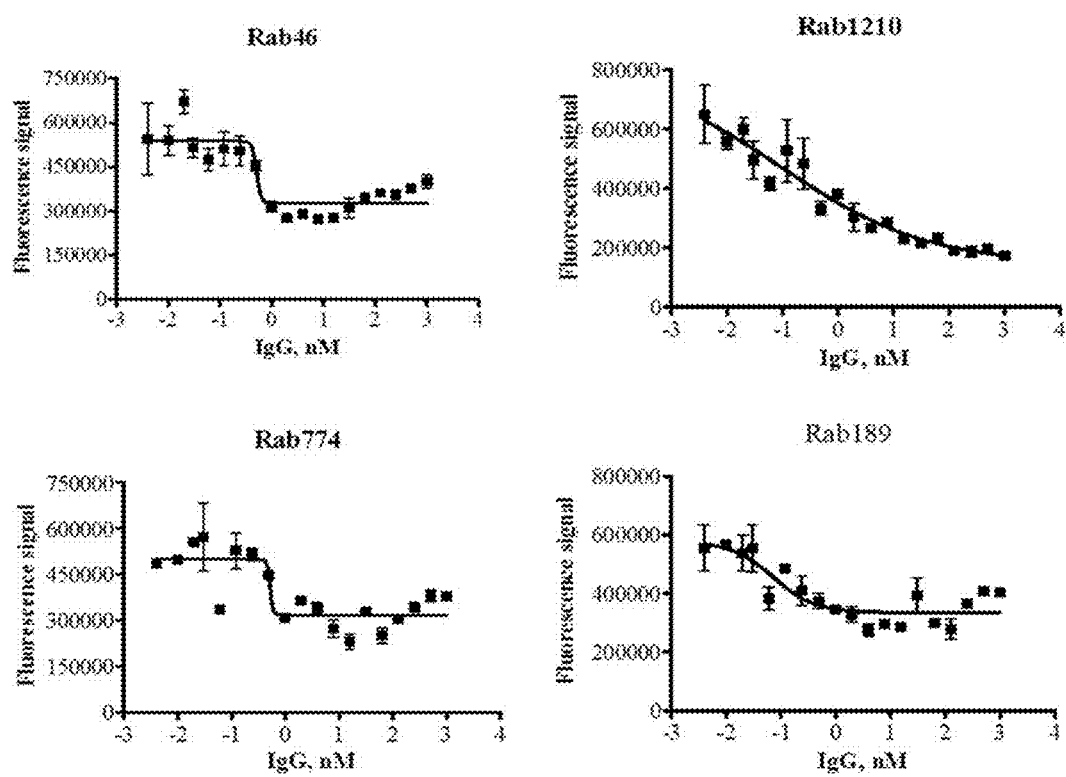
FIG. 6. Ligand blocking assay using alpha screening format and graphs show dose response of anti-HER3 antibodies.

HER3 ligand neuregulin (NRG1) can bind on HER3 extracellular domain and activates HER3 phosphorylation and down-stream signaling. Blocking ligand binding on HER3 by the selected rabbit HER3 monoclonal antibodies was determined using alpha screen format assay. NRG1 (R&D Systems) was biotinylated using a biotinylation kit (Fisher Scientific) and HER3 ECD was tagged with 10 histidine (His). Purified anti-HER3 Mabs were serially diluted two-fold into an assay buffer made from 25 mM Hepes, 100 mM NaCl, 0.5% BSA and 0.05% Tween20 in an opaque/white, half-well area plate (Costar). Rabbit IgG1 was used as a negative control. Biotinylated NRG-lbeta ligand and Her3/$His_{10}$ receptor were added sequentially at 10 nM concentration to the assay plate containing serially diluted antibodies. The mixture of receptor, ligand and the antibodies was incubated at room temperature with gentle shaking for 90 minutes. AlphaScreen Streptavidin Donor beads and His-Nickel Acceptor beads were added into the assay at a final concentration of 20 µg/ml each. The assay plates were covered with foil and incubated at room temperature with gentle shaking for 1 hour. The plates were read in EnVision plate reader. Blocking of NRG1 ligand binding to HER3 by the HER3 monoclonal antibodies showed concentration dependence (FIG. 6) and $IC_{50}$ values (Table 4) were estimated using four parameter curve fitting with concentration titration graphs using the GraphPad.

TABLE 4

IC50 estimated from dose dependence titration curves for inhibition of pHER3, inhibition of pAKT, inhibition of pERK, and NRG ligand binding by anti-HER3 antibodies

| HER3 monoclonal antibody | pHER3 inhibition, EC50 (nM) | pAKT inhibition, EC50 (nM) | pERK1/2 inhibition, EC50 (nM) | Blocking NRG binding, EC50 (nM) |
|---|---|---|---|---|
| Rab46 | 3.5 | 3.8 | 6.2 | 0.51 |
| Rab1210 | 0.7 | 0.4 | 1.3 | 0.10 |
| Rab189 | 1.7 | 3.6 | 5.5 | 0.07 |
| Rab774 | 1.8 | 2.3 | 3.8 | 0.52 |

Example 7

Inhibition of Cancer Cell Proliferation by Anti-HER3 mAbs

Figure 7:
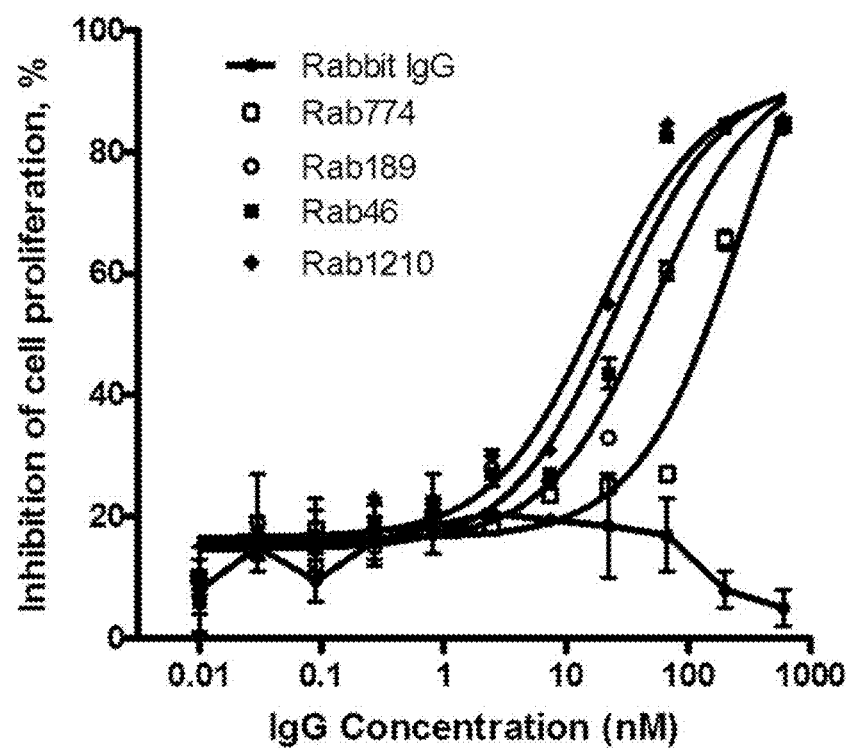
FIG. 7. Inhibition of NRG-induced cell growth in MCF7 cells by anti HER3 antibodies. Data are shown as percentage of reduction by the antibodies relative to no antibody control.

In order to determine inhibition of cancer cell proliferation by the isolated HER3 antibodies, 3000 cells/well of MCF7 (human breast cancer) cancer cells were seeded in 100 µl of 10% FBS medium on 96-well a 37° C. incubator overnight. The medium was replaced with 0.5% FBS medium with HER3 antibodies and were cultured for 72 hours with stimulation with 100 ng/ml β-NRG by adding the ligand directly to antibody containing medium. Cell proliferation was measured by adding 10 µl of AlamarBlum™ (Invitrogen) added to the medium and the cells were incubated at 37° C. incubator and fluorescence signals were measured after two hours after addition of AlamarBlum™ at excitation 535 nm and emission at 590 nm. Inhibition of NRG-induced cell growth in MCF7 cells was calculated as percentage of reduction by the antibodies relative to no antibody treatment (FIG. 7) and $IC_{50}$ values are listed in Table 5.

TABLE 5

IC50 of inhibition of cancer cell proliferation by anti-HER3 monoclonal antibodies

| HER3 monoclonal antibody | IC50 (95% confidence level), nM |
|---|---|
| Rab46 | 15.28 to 42.28 |
| Rab1210 | 11.92 to 28.53 |
| Rab189 | 31.66 to 86.07 |
| Rab774 | 151.2 to 526.7 |

Example 8

Sequencing Antibody Variable Region of DNA and Amino Acid Sequences

IgG light chain variable region (LV) and heavy chain variable region (HV) were sequenced by Genewiz (Edison, N.J.). Both light chain variable and heavy chain variable amino acid sequences are listed Table 6. CDRs of light chain and heavy chain were analyzed using IMGT program and are listed in Table 6.

TABLE 6

Anti-HER3 antibody sequences

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| Rab46 | GFSFSASY Y (SEQ ID NO: 9) | ITGDDDKR T (SEQ ID NO: 10) | TRNLPDEL (SEQ ID NO: 11) | ESVYSYKN (SEQ ID NO: 12) | QAS (SEQ ID NO: 13) | QGTYYSSA WDFV (SEQ ID NO: 14) |
| | EEQLVESGGGLVQPEGSLTLTCTAS<u>GF SFSASYY</u>IYWVRQAPGKGLEGIAY<u>ITG DDDKR</u>TYYANWAKGRFTISKTSTTVTL QMTSLTAADTATYFC<u>TRNLPDEL</u>WGPG TLVTVSS (SEQ ID NO: 1) | | | QAVVTQTPSSVSAAVGGTVTISCQSS<u>E SVYSYKN</u>LAWYQQKPGQPPRLLIW<u>QAS</u> RLSSGVSSRFSGSGSGTQFTLTISGVQ CDDAATYYC<u>QGTYYSSAWDF</u>VFGGGTE VMVE (SEQ ID NO: 2) | | |
| Rab1210 | GFSFSSSY W (SEQ ID NO: 15) | IWSGNGAT (SEQ ID NO: 16) | ARNYDASG YGIFHL (SEQ ID NO: 17) | QSIVSSY (SEQ ID NO: 18) | SAS (SEQ ID NO: 19) | LYGVDSSN IDNA (SEQ ID NO: 20) |
| | QEQLEESGGGLVQPEGSLTLTCTAS<u>GF SFSSSYW</u>ICWVRQAPGKGLELIGY<u>IWS GNGAT</u>YYASWAKGRFTISKTSSTTVTL QMTSVTATDTATYFC<u>ARNYDASGYGIF HL</u>WGPGTLVTVSS (SEQ ID NO: 3) | | | QAVVMTQTPASVSAAVGGTVTINCQAS <u>QSIVSSY</u>LSWYQQKTGQPPKLLIY<u>SAS</u> KLASGVPPRFSGSGSGTQFTLTISGVQ CDDAATYYC<u>LYGVDSSNIDNA</u>FGGGTE VVVK (SEQ ID NO: 4) | | |
| Rab189 | GIGFGYYY Y (SEQ ID NO: 21) | IYTGISDS T (SEQ ID NO: 22) | ARSDPYYT TTYTNTYP TYWNL (SEQ ID NO: 23) | QSINNY (SEQ ID NO: 24) | RAS (SEQ ID NO: 25) | QSYYYSSS NNYYNA (SEQ ID NO: 26) |
| | QESLEESGGDLVKPEGTLTLICKAS<u>GI GFGYYYY</u>ICWVRQAPGKGLEWIAC<u>IYT GISDS</u>TYYATWAKGRFAISKTSSTTVT LQMTSLTAADTATYFC<u>ARSDPYYTTTY TNTYPTYWNL</u>WGPGTLVTVSS (SEQ ID NO: 5) | | | CAFELTQTPSSVEAAVGGTVTIKCQAS <u>QSINNY</u>LAWYQQKTGQPPKLLIY<u>RAST</u> LESGVPSRFKGSGSGTQFTLTISDLEC ADAATYYC<u>QSYYYSSSNNYYNA</u>FGGGT EVVVK (SEQ ID NO: 6) | | |
| Rab774 | GIDLSTYA (SEQ ID NO: 27) | INRSSKT (SEQ ID NO: 28) | GRVMSPYS VAGGDL (SEQ ID NO: 29) | SDLSDYT (SEQ ID NO: 30) | LRSDGSY (SEQ ID NO: 31) | GLPYSVEY V (SEQ ID NO: 32) |
| | QSVEESGGRLVTPGTPLTLTCTVS<u>GID LSTYA</u>MTWVRRAPGKGLEWLGI<u>INRSS KT</u>YLTDWARGRFTISKTSTTVDLKISS PTTEDTATYFC<u>GRVMSPYSVAGGDL</u>WG PGTLVTVSS (SEQ ID NO: 7) | | | QPVLTQSPSASAALGASAKLTCILS<u>SD LSDYT</u>IDWYKHQQGEAPRYLMQ<u>LRSDG SY</u>TKGTGVPDRFSGSSSGADRYLVISS VQADDEADYYC<u>GLPYSVEYV</u>FGGGTQL TVT (SEQ ID NO: 8) | | |

Example 9

Humanization of Rabbit HER3 Monoclonal Antibodies

The best matched human VH and VL germline sequences to the rabbit VH and VL sequences were identified using the IMGT data base (Lafranc et al., 2012, incorporated herein by reference). Humanization was based on the CDR grafting concept (Haidar et al., 2012) and CDRs of the rabbit antibodies were defined by the combination of Kabat/Chothia, Yu et al., 2010 and Haidar et al. 2012 (See also Retter et al., 2005 and Singer et al., 1993).

Total of 2 heavy chains and 2 light chains of variable sequences were designed for each of anti-HER3 monoclonal antibodies: Rab46 and Rab1210 as shown below in Chart 1 (CDR sequences are underlined).

CHART 1

Variable domains of humanized antibodies.

>hRab46H-1
QVQLVESGGGLVQPGGSLRLSCSAS<u>GFSFSASYY</u>IYWVRQAPGKGLEYIA
<u>YITGDDDKR</u>TYYANWAKGRFTISRDNSKNTVYLQMNSLRAEDTAVYYC
<u>TRNLPDEL</u>WGPGTLVTVSS (SEQ ID NO: 33)

>hRab46H-2
QVQLVESGGGLVQPGGSLRLSCSAS<u>GFSFSASYY</u>IYWVRQAPGKGLEYIA
<u>YITGDDDKR</u>TYYANWAKGRFTISRDTSKNTVYLQMNSLRAEDTAVYYC<u>T
RNLPDEL</u>WGPGTLVTVSS (SEQ ID NO: 34)

CHART 1-continued

Variable domains of humanized antibodies.

>hRab46L-1
DIQMTQTPSTLSASVGDRVTITCQSS<u>ESVYSYKN</u>LAWYQQKPGKPPKLLI
W<u>QA</u>SRLSSGVPSRFSGSGSGTEFTLTISSLQPDDFATYYC<u>QGTYYSSAWDF</u>
<u>V</u>FGGGTKVEIK (SEQ ID NO: 35)

>hRab46L-2
QAQMTQTPSTLSASVGDRVTITCQSS<u>ESVYSYKN</u>LAWYQQKPGKPPKLLI
W<u>QA</u>SRLSSGVPSRFSGSGSGTEFTLTISSLQPDDFATYYC<u>QGTYYSSAWDF</u>
<u>V</u>FGGGTKVEIK (SEQ ID NO: 36)

>hRab1210H-1
QVQLVESGGGLVQPGGSLRLSCSAS<u>GFSFSSSYW</u>ICWVRQAPGKGLEYIG
Y<u>IWSGNGATY</u>YASWAKGRFTISRDNSKNTVYLQMNSLRAEDTAVYFC<u>A</u>
<u>RNYDASGYGIFHL</u>WGPGTLVTVSS (SEQ ID NO: 37)

>hRab1210H-2
QVQLVESGGGLVQPGGSLRLSCSAS<u>GFSFSSSYW</u>ICWVRQAPGKGLELIG
Y<u>IWSGNGATY</u>YASWAKGRFTISRDTSKNTVYLQMNSLRAEDTAVYFC<u>AR</u>
<u>NYDASGYGIFHL</u>WGPGTLVTVSS (SEQ ID NO: 38)

>hRab1210L-1
DIQMTQTPSSLSASVGDRVTINCQAS<u>QSIVSSY</u>LSWYQQKPGKPPKLLIY<u>S</u>
<u>ASKLA</u>SGVPSRFSGSGSGTDFTLTISSLQPEDFATYYC<u>LYGVDSSNIDNAF</u>
GGGTKVEIK (SEQ ID NO: 39)

>hRab1210L-2
AVQMTQTPSSLSASVGDRVTINCQAS<u>QSIVSSY</u>LSWYQQKPGKPPKLLIY<u>S</u>
<u>ASKLA</u>SGVPSRFSGSGSGTDFTLTISSLQPEDFATYYC<u>LYGVDSSNIDNAF</u>
GGGTKVEIK (SEQ ID NO: 40)

Construction and Production of Humanized Monoclonal Antibodies

The DNA sequences from the designed humanized variable regions were synthesized and cloned into IgG1 expression vectors as described in the previous examples for production of the humanized antibodies in HEK293 cells. Total of 8 humanized monoclonal antibodies were produced by recombination of 1 heavy chain and 1 light chain in each of antibodies. The composition of heavy and light chains for each of humanized antibodies is listed in the Table 8 below.

TABLE 8

Heavy and light chain variable regions of the humanized HER3 mAb.

| Name of Humanized Antibody | Parental Clone Name | Heavy Chain Variable Sequences | Light Chain Variable Sequences |
|---|---|---|---|
| HER3-hMab-A9 | Rab46 | hRab46H-1 | hRab46L-1 |
| HER3-hMab-A10 | Rab46 | hRab46H-2 | hRab46L-1 |
| HER3-hMab-A11 | Rab46 | hRab46H-1 | hRab46L-2 |
| HER3-hMab-A12 | Rab46 | hRab46H-2 | hRab46L-2 |
| HER3-hMab-A13 | Rab1210 | hRab1210H-1 | hRab1210L-1 |
| HER3-hMab-A14 | Rab1210 | hRab1210H-2 | hRab1210L-1 |
| HER3-hMab-A15 | Rab1210 | hRab1210H-1 | hRab1210L-2 |
| HER3-hMab-A16 | Rab1210 | hRab1210H-2 | hRab1210L-2 |

Characterization of Humanized Anti-HER3 Monoclonal Antibodies

Binding of the humanized HER3 monoclonal antibodies on extracellular domain (ECD) of HER3 by ELISA: All monoclonal antibodies showed strong binding on human HER3 ECD similar to the parental rabbit monoclonal antibodies, as shown in FIG. 8A. For the panel of 4 humanized antibodies from the parental Rab46, all 4 antibodies retained binding affinity on mouse HER3 ECD domains (FIG. 8B). The estimated EC50s (concentrations give 50% of maximum binding capacity) for those humanized antibodies are listed in Table 9.

TABLE 9

$EC_{50}$s (μg/ml) of humanized HER3 antibodies by ELISA.

| HER3 Antigen | A9 | A10 | A11 | A12 | A13 | A14 | A15 | A16 | Chi46 | Chi1210 |
|---|---|---|---|---|---|---|---|---|---|---|
| Human HER3 ECD | 0.0031 | 0.0026 | 0.0026 | 0.0024 | 0.0025 | 0.0019 | 0.0024 | 0.0023 | 0.0027 | 0.0026 |
| Mouse HER3 ECD | 0.0043 | 0.0054 | 0.0079 | 0.0067 | 0.0059 | | | | | |

HER3 antigen binding kinetics of the humanized HER3 antibodies measured by surface Plasmon resonance (SPR) method: Kinetic constants of the antibodies were determined using a T-100 Biacore instrument (Table 10). SPR sensorgrams of the humanized HER3 antibodies and their parental rabbit/human Fc chimeras are shown in FIG. 9.

TABLE 10

Kinetic binding constants for humanized HER3 antibodies.

| Antibody | ka (1/Ms) | kd (1/s) | KD (M) |
|---|---|---|---|
| A10 | 1.41E+05 | 1.69E−04 | 1.20E−09 |
| A14 | 2.01E+05 | 1.74E−04 | 8.62E−10 |
| CHI46 | 1.38E+05 | 4.58E−04 | 3.32E−09 |
| CHI1210 | 5.38E+05 | 6.44E−04 | 1.20E−09 |

Inhibition of HER3 phosphorylation by humanized HER3 monoclonal antibodies: Assay of HER3 signaling inhibition was conducted as described for rabbit HER3 antibodies in the earlier section. As shown in FIG. 10, the humanized HER3 antibodies, A10 and A14, showed equal to better inhibition of HER3 phosphorylation than their parental antibodies. Estimated $IC_{50}$ of pHER3 inhibition from the concentration titration graphs (FIG. 10) is shown in Table 11.

TABLE 11

Estimated $IC_{50}$ for inhibition of pHER3 by the humanized HER3 antibodies.

| Antibody Name | A10 | A14 | Chi46 | Chi1210 |
|---|---|---|---|---|
| pHER3 inhibition ($IC_{50}$, μg/ml) | 0.0173 | 0.0017 | 0.0330 | 0.0035 |

Inhibition of cancer cell proliferation by the humanized HER3 monoclonal antibodies: Inhibition of cancer cell proliferation was determined using the same procedures as described for studies with the rabbit monoclonal antibodies. Two cancer cell lines were used, one is breast cancer cell line MCF-7 and the other cell line is the prostate cancer cell line CWR22, and both cell lines were from the ATCC (American Tissue Culture Collection). Inhibition of cancer cell proliferations showed positive correlation with the increased antibody concentrations as shown in FIGS. 11 and 12. The estimated $IC_{50}$ for inhibition of cancer cell proliferation is shown in Table 12.

TABLE 5

Estimated $IC_{50}$ for inhibition of cancer cell proliferation by the humanized HER3 antibodies.

| Antibody Name | A10 | A14 | Chi46 | Chi1210 |
|---|---|---|---|---|
| Inhibition of MCF-7 cancer cell proliferation ($IC_{50}$, μg/ml) | 0.181 | 0.232 | ND* | 0.084 |
| Inhibition of CWR22 cancer cell proliferation ($IC_{50}$, μg/ml) | 0.036 | 0.025 | 0.138 | 0.003 |

*ND, not determined

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application Nos. 2002/0172677; 2004/0126828; and 20050214860
U.S. Patent Nos. 3/817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,091,513; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,881,557; 6,891,024; and 6,946,546.
Hu et al., Cancer Res., 56, 3055-3061, 1996
Liu et al. Cell Mol. Biol., 49(2):209-216, 2003
Marks, et al., J. Biol. Chem. 267:16007-16010 1992
Stemmer, Nature, vol. 370, p. 389-391, 1994;
Gram et al. Proc. Natl. Acad. Sci., USA, 89:3576-3580, 1992
Barbas et al., Proc. Natl. Acad. Sci., USA, 91:3809-3813, 1994
Schier et al. J. Mol. Biol. 263:551-567, 1996.
Haidar et al. A universal combinatorial design of antibody framework to graft distinct CDR sequences: a bioinformatics approach. Proteins 80, 896-912, 2012.
Yu et al. A humanized anti-VEGF rabbit monoclonal antibody inhibits angiogenesis and blocks tumor growth in xenograft models. PloS one 5, 2010.
Retter et al., VBASE2, an integrative V gene database. Nucleic acids research 33, D671-674, 2005.
Lefranc et al., Use of IMGT((R)) databases and tools for antibody engineering and humanization. *Methods in molecular biology* 907, 3-37, 2012.
Singer et al., Optimal humanization of 1B4, an anti-CD18 murine monoclonal antibody, is achieved by correct choice of human V-region framework sequences. *Journal of immunology* 150, 2844-2857, 1993.
Ridderet al., Generation of rabbit immune libraries In Antibody Engineering, Eds by Kontermann, R. and Dubel, S. Springer publisher, 2001

What is claimed is:

1. A method for treating a subject having a HER3-positive cancer comprising administering an effective amount of an antibody to the subject, wherein the antibody comprises:
   (i) a $V_H$ domain at least about 80% identical to the $V_H$ domain of Rab46 (SEQ ID NO: 1); hRab46H-1 (SEQ ID NO: 33); or hRab46H-2 (SEQ ID NO: 34), wherein said $V_H$ domain comprises CDRs 1-3 of SEQ ID NOS: 9-11; and a $V_L$ domain at least about 80% identical to the $V_L$ domain of Rab46 (SEQ ID NO: 2); hRab46L-1 (SEQ ID NO: 35); or hRab46L-2 (SEQ ID NO: 36), wherein said VL domain comprises CDRs 1-3 of SEQ ID NOS: 12-14;
   (ii) a $V_H$ domain at least about 80% identical to the $V_H$ domain of Rab1210 (SEQ ID NO: 3); hRab1210H-1 (SEQ ID NO: 37); or hRab1210H-2 (SEQ ID NO: 38), wherein said $V_H$ domain comprises CDRs 1-3 of SEQ ID NOS: 15-17; and a $V_L$ domain at least about 80% identical to the $V_L$ domain of Rab1210 (SEQ ID NO: 4); hRab1210L-1 (SEQ ID NO: 39); or hRab1210L-2 (SEQ ID NO: 40), wherein said $V_L$ domain comprises CDRs 1-3 of SEQ ID NOS: 18-20;
   (iii) a $V_H$ domain at least about 80% identical to the $V_H$ domain of Rab189 (SEQ ID NO: 5), wherein said $V_H$ domain comprises CDRs 1-3 of SEQ ID NOS: 21-23; and a $V_L$ domain at least about 80% identical to the $V_L$ domain of Rab189 (SEQ ID NO: 6), wherein said $V_L$ domain comprises CDRs 1-3 of SEQ ID NOS: 24-26; or
   (iv) a $V_H$ domain at least about 80% identical to the $V_H$ domain of Rab774 (SEQ ID NO: 7), wherein said $V_H$ domain comprises CDRs 1-3 of SEQ ID NOS: 27-29; and a $V_L$ domain at least about 80% identical to the $V_L$ domain of Rab774 (SEQ ID NO: 8), wherein said $V_L$ domain comprises CDRs 1-3 of SEQ ID NOS: 30-32.

2. The method of claim 1, wherein the HER3-postive cancer is a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer.

3. The method of claim 1, wherein the antibody is in a pharmaceutically acceptable composition.

4. The method of claim 1, wherein the antibody is administered systemically.

5. The method of claim 1, wherein the antibody is administered intravenously, intradermally, intratumorally, intramuscularly, intraperitoneally, subcutaneously, or locally.

6. The method of claim 1, further comprising administering at least a second anticancer therapy to the subject.

7. The method of claim 6, wherein the second anticancer therapy is a surgical therapy, chemotherapy, radiation therapy, cryotherapy, hormonal therapy, immunotherapy or cytokine therapy.

8. The method of claim 1, wherein the antibody comprises a $V_H$ domain at least 95% identical to the $V_H$ domain of hRab46H-1 (SEQ ID NO: 33) and a $V_L$ domain at least 95% identical to the $V_L$ domain of hRab46L-1 (SEQ ID NO: 35) or hRab46L-2 (SEQ ID NO: 36).

9. The method of claim 8, wherein the antibody comprises a $V_H$ domain identical to the $V_H$ domain of hRab46H-1 (SEQ ID NO: 33) and a $V_L$ domain identical to the $V_L$ domain of hRab46L-1 (SEQ ID NO: 35).

10. The method of claim 8, wherein the antibody comprises a $V_H$ domain identical to the $V_H$ domain of hRab46H-1 (SEQ ID NO: 33) and a $V_L$ domain identical to the $V_L$ domain hRab46L-2 (SEQ ID NO: 36).

11. The method of claim 1, wherein the antibody comprises a $V_H$ domain at least 95% identical to the $V_H$ domain of hRab46H-2 (SEQ ID NO: 34) and a $V_L$ domain at least 95% identical to the $V_L$ domain of hRab46L-2 (SEQ ID NO: 36) or hRab46L-1 (SEQ ID NO: 35).

12. The method of claim 11, wherein the antibody comprises a $V_H$ domain identical to the $V_H$ domain of hRab46H-2 (SEQ ID NO: 34) and a $V_L$ domain identical to the $V_L$ domain of hRab46L-2 (SEQ ID NO: 36).

13. The method of claim 11, wherein the antibody comprises a $V_H$ domain identical to the $V_H$ domain of hRab46H-2 (SEQ ID NO: 34) and a $V_L$ domain identical to the $V_L$ domain of hRab46L-1 (SEQ ID NO: 35).

14. The method of claim 1, wherein the antibody comprises a $V_H$ domain at least 95% identical to the $V_H$ domain of hRab1210H-1 (SEQ ID NO: 37) and a $V_L$ domain at least 95% identical to the $V_L$ domain of hRab1210L-1 (SEQ ID NO: 39) or hRab1210L-2 (SEQ ID NO: 40).

15. The method of claim 14, wherein the antibody comprises a $V_H$ domain identical to the $V_H$ domain of hRab1210H-1 (SEQ ID NO: 37) and a $V_L$ domain identical to the $V_L$ domain of hRab1210L-1 (SEQ ID NO: 39).

16. The method of claim 14, wherein the antibody comprises a $V_H$ domain identical to the $V_H$ domain of hRab1210H-1 (SEQ ID NO: 37) and a $V_L$ domain identical to the $V_L$ domain of hRab1210L-2 (SEQ ID NO: 40).

17. The method of claim 1, wherein the antibody comprises a $V_H$ domain at least 95% identical to the $V_H$ domain of hRab1210H-2 (SEQ ID NO: 38) and a $V_L$ domain at least 95% identical to the $V_L$ domain of hRab1210L-2 (SEQ ID NO: 40) or hRab1210L-1 (SEQ ID NO: 39).

18. The method of claim 17, wherein the antibody comprises a $V_H$ domain identical to the $V_H$ domain of hRab1210H-2 (SEQ ID NO: 38) and a $V_L$ domain identical to the $V_L$ domain of hRab1210L-2 (SEQ ID NO: 40).

19. The method of claim 17, wherein the antibody comprises a $V_H$ domain identical to the $V_H$ domain of hRab1210H-2 (SEQ ID NO: 38) and a $V_L$ domain identical to the $V_L$ domain of hRab1210L-1 (SEQ ID NO: 39).

20. The method of claim 17, wherein the antibody is the HER3-hMab-A9, HER3-hMab-A10, HER3-hMab-A11, HER3-hMab-A12, HER3-hMab-A13, HER3-hMab-A14, HER3-hMab-A15 or HER3-hMab-A16 antibody.

* * * * *

SEQUENCE LISTING

```
<160> NUMBER OF SEQ ID NOS: 52

<210> SEQ ID NO 1
<211> LENGTH: 115
<212> TYPE: PRT
<213> ORGANISM: Artificial Sequence
<220> FEATURE:
<223> OTHER INFORMATION: Monoclonal antibody fragment

<400> SEQUENCE: 1

Glu Glu Gln Leu Val Glu Ser Gly Gly Gly Leu Val Gln Pro Glu Gly
1               5                   10                  15
```

-continued

Ser Leu Thr Leu Thr Cys Thr Ala Ser Gly Phe Ser Phe Ala Ser
            20                  25                  30

Tyr Tyr Ile Tyr Trp Val Arg Gln Ala Pro Gly Lys Gly Leu Glu Gly
        35                  40                  45

Ile Ala Tyr Ile Thr Gly Asp Asp Lys Arg Thr Tyr Tyr Ala Asn
50                  55                  60

Trp Ala Lys Gly Arg Phe Thr Ile Ser Lys Thr Ser Thr Thr Val Thr
65                  70                  75                  80

Leu Gln Met Thr Ser Leu Thr Ala Ala Asp Thr Ala Thr Tyr Phe Cys
                85                  90                  95

Thr Arg Asn Leu Pro Asp Glu Leu Trp Gly Pro Gly Thr Leu Val Thr
            100                 105                 110

Val Ser Ser
    115

<210> SEQ ID NO 2
<211> LENGTH: 112
<212> TYPE: PRT
<213> ORGANISM: Artificial Sequence
<220> FEATURE:
<223> OTHER INFORMATION: Monoclonal antibody fragment

<400> SEQUENCE: 2

Gln Ala Val Val Thr Gln Thr Pro Ser Ser Val Ser Ala Ala Val Gly
1               5                   10                  15

Gly Thr Val Thr Ile Ser Cys Gln Ser Ser Glu Ser Val Tyr Ser Tyr
            20                  25                  30

Lys Asn Leu Ala Trp Tyr Gln Gln Lys Pro Gly Gln Pro Pro Arg Leu
        35                  40                  45

Leu Ile Trp Gln Ala Ser Arg Leu Ser Ser Gly Val Ser Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Thr Tyr Tyr Ser
                85                  90                  95

Ser Ala Trp Asp Phe Val Phe Gly Gly Gly Thr Glu Val Met Val Glu
            100                 105                 110

<210> SEQ ID NO 3
<211> LENGTH: 121
<212> TYPE: PRT
<213> ORGANISM: Artificial Sequence
<220> FEATURE:
<223> OTHER INFORMATION: Monoclonal antibody fragment

<400> SEQUENCE: 3

Gln Glu Gln Leu Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Tyr Trp Ile Cys Trp Val Arg Gln Ala Pro Gly Lys Gly Leu Glu Leu
        35                  40                  45

Ile Gly Tyr Ile Trp Ser Gly Asn Gly Ala Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Val Thr Ala Thr Asp Thr Ala Thr Tyr Phe Cys
                85                  90                  95

```
Ala Arg Asn Tyr Asp Ala Ser Gly Tyr Gly Ile Phe His Leu Trp Gly
            100                 105                 110

Pro Gly Thr Leu Val Thr Val Ser Ser
        115                 120

<210> SEQ ID NO 4
<211> LENGTH: 112
<212> TYPE: PRT
<213> ORGANISM: Artificial Sequence
<220> FEATURE:
<223> OTHER INFORMATION: Monoclonal antibody fragment

<400> SEQUENCE: 4

Gln Ala Val Val Met Thr Gln Thr Pro Ala Ser Val Ser Ala Ala Val
1               5                   10                  15

Gly Gly Thr Val Thr Ile Asn Cys Gln Ala Ser Gln Ser Ile Val Ser
            20                  25                  30

Ser Tyr Leu Ser Trp Tyr Gln Gln Lys Thr Gly Gln Pro Pro Lys Leu
        35                  40                  45

Leu Ile Tyr Ser Ala Ser Lys Leu Ala Ser Gly Val Pro Pro Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Tyr Gly Val Asp Ser
                85                  90                  95

Ser Asn Ile Asp Asn Ala Phe Gly Gly Gly Thr Glu Val Val Val Lys
            100                 105                 110

<210> SEQ ID NO 5
<211> LENGTH: 129
<212> TYPE: PRT
<213> ORGANISM: Artificial Sequence
<220> FEATURE:
<223> OTHER INFORMATION: Monoclonal antibody fragment

<400> SEQUENCE: 5

Gln Glu Ser Leu Glu Glu Ser Gly Gly Asp Leu Val Lys Pro Glu Gly
1               5                   10                  15

Thr Leu Thr Leu Thr Cys Lys Ala Ser Gly Ile Gly Phe Gly Tyr Tyr
            20                  25                  30

Tyr Tyr Ile Cys Trp Val Arg Gln Ala Pro Gly Lys Gly Leu Glu Trp
        35                  40                  45

Ile Ala Cys Ile Tyr Thr Gly Ile Ser Asp Ser Thr Tyr Tyr Ala Thr
    50                  55                  60

Trp Ala Lys Gly Arg Phe Ala Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ser Asp Pro Tyr Thr Thr Tyr Thr Thr Asn Thr Tyr
            100                 105                 110

Pro Thr Tyr Trp Asn Leu Trp Gly Pro Gly Thr Leu Val Thr Val Ser
        115                 120                 125

Ser

<210> SEQ ID NO 6
<211> LENGTH: 113
<212> TYPE: PRT
<213> ORGANISM: Artificial Sequence
```

```
<220> FEATURE:
<223> OTHER INFORMATION: Monoclonal antibody fragment

<400> SEQUENCE: 6

Cys Ala Phe Glu Leu Thr Gln Thr Pro Ser Ser Val Glu Ala Ala Val
1               5                   10                  15

Gly Gly Thr Val Thr Ile Lys Cys Gln Ala Ser Gln Ser Ile Asn Asn
            20                  25                  30

Tyr Leu Ala Trp Tyr Gln Gln Lys Thr Gly Gln Pro Pro Lys Leu Leu
        35                  40                  45

Ile Tyr Arg Ala Ser Thr Leu Glu Ser Gly Val Pro Ser Arg Phe Lys
50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Ser Tyr Tyr Tyr Ser Ser
                85                  90                  95

Ser Asn Asn Tyr Tyr Asn Ala Phe Gly Gly Gly Thr Glu Val Val Val
            100                 105                 110

Lys

<210> SEQ ID NO 7
<211> LENGTH: 117
<212> TYPE: PRT
<213> ORGANISM: Artificial Sequence
<220> FEATURE:
<223> OTHER INFORMATION: Monoclonal antibody fragment

<400> SEQUENCE: 7

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Ala
            20                  25                  30

Met Thr Trp Val Arg Arg Ala Pro Gly Lys Gly Leu Glu Trp Leu Gly
        35                  40                  45

Ile Ile Asn Arg Ser Ser Lys Thr Tyr Leu Thr Asp Trp Ala Arg Gly
50                  55                  60

Arg Phe Thr Ile Ser Lys Thr Ser Thr Val Asp Leu Lys Ile Ser
65                  70                  75                  80

Ser Pro Thr Thr Glu Asp Thr Ala Thr Tyr Phe Cys Gly Arg Val Met
                85                  90                  95

Ser Pro Tyr Ser Val Ala Gly Gly Asp Leu Trp Gly Pro Gly Thr Leu
            100                 105                 110

Val Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Monoclonal antibody fragment

<400> SEQUENCE: 8

Gln Pro Val Leu Thr Gln Ser Pro Ser Ala Ser Ala Ala Leu Gly Ala
1               5                   10                  15

Ser Ala Lys Leu Thr Cys Ile Leu Ser Ser Asp Leu Ser Asp Tyr Thr
            20                  25                  30

Ile Asp Trp Tyr Lys His Gln Gln Gly Glu Ala Pro Arg Tyr Leu Met
```

```
                35                  40                  45
Gln Leu Arg Ser Asp Gly Ser Tyr Thr Lys Gly Thr Gly Val Pro Asp
         50                  55                  60
Arg Phe Ser Gly Ser Ser Ser Gly Ala Asp Arg Tyr Leu Val Ile Ser
 65                  70                  75                  80
Ser Val Gln Ala Asp Asp Glu Ala Asp Tyr Tyr Cys Gly Leu Pro Tyr
                 85                  90                  95
Ser Val Glu Tyr Val Phe Gly Gly Gly Thr Gln Leu Thr Val Thr
            100                 105                 110

<210> SEQ ID NO 9
<211> LENGTH: 9
<212> TYPE: PRT
<213> ORGANISM: Artificial Sequence
<220> FEATURE:
<223> OTHER INFORMATION: Monoclonal antibody fragment

<400> SEQUENCE: 9

Gly Phe Ser Phe Ser Ala Ser Tyr Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Monoclonal antibody fragment

<400> SEQUENCE: 10

Ile Thr Gly Asp Asp Asp Lys Arg Thr
1               5

<210> SEQ ID NO 11
<211> LENGTH: 8
<212> TYPE: PRT
<213> ORGANISM: Artificial sequence
<220> FEATURE:
<223> OTHER INFORMATION: Monoclonal antibody fragment

<400> SEQUENCE: 11

Thr Arg Asn Leu Pro Asp Glu Leu
1               5

<210> SEQ ID NO 12
<211> LENGTH: 8
<212> TYPE: PRT
<213> ORGANISM: Artificial sequence
<220> FEATURE:
<223> OTHER INFORMATION: Monoclonal antibody fragment

<400> SEQUENCE: 12

Glu Ser Val Tyr Ser Tyr Lys Asn
1               5

<210> SEQ ID NO 13
<211> LENGTH: 3
<212> TYPE: PRT
<213> ORGANISM: Artificial sequence
<220> FEATURE:
<223> OTHER INFORMATION: Monoclonal antibody fragment

<400> SEQUENCE: 13

Gln Ala Ser
1
```

```
<210> SEQ ID NO 14
<211> LENGTH: 12
<212> TYPE: PRT
<213> ORGANISM: Artificial sequence
<220> FEATURE:
<223> OTHER INFORMATION: Monoclonal antibody fragment

<400> SEQUENCE: 14

Gln Gly Thr Tyr Tyr Ser Ser Ala Trp Asp Phe Val
1               5                   10

<210> SEQ ID NO 15
<211> LENGTH: 9
<212> TYPE: PRT
<213> ORGANISM: Artificial sequence
<220> FEATURE:
<223> OTHER INFORMATION: Monoclonal antibody fragment

<400> SEQUENCE: 15

Gly Phe Ser Phe Ser Ser Ser Tyr Trp
1               5

<210> SEQ ID NO 16
<211> LENGTH: 8
<212> TYPE: PRT
<213> ORGANISM: Artificial sequence
<220> FEATURE:
<223> OTHER INFORMATION: Monoclonal antibody fragment

<400> SEQUENCE: 16

Ile Trp Ser Gly Asn Gly Ala Thr
1               5

<210> SEQ ID NO 17
<211> LENGTH: 14
<212> TYPE: PRT
<213> ORGANISM: Artificial sequence
<220> FEATURE:
<223> OTHER INFORMATION: Monoclonal antibody fragment

<400> SEQUENCE: 17

Ala Arg Asn Tyr Asp Ala Ser Gly Tyr Gly Ile Phe His Leu
1               5                   10

<210> SEQ ID NO 18
<211> LENGTH: 7
<212> TYPE: PRT
<213> ORGANISM: Artificial sequence
<220> FEATURE:
<223> OTHER INFORMATION: Monoclonal antibody fragment

<400> SEQUENCE: 18

Gln Ser Ile Val Ser Ser Tyr
1               5

<210> SEQ ID NO 19
<211> LENGTH: 3
<212> TYPE: PRT
<213> ORGANISM: Artificial sequence
<220> FEATURE:
<223> OTHER INFORMATION: Monoclonal antibody fragment

<400> SEQUENCE: 19

Ser Ala Ser
1
```

```
<210> SEQ ID NO 20
<211> LENGTH: 12
<212> TYPE: PRT
<213> ORGANISM: Artificial sequence
<220> FEATURE:
<223> OTHER INFORMATION: Monoclonal antibody fragment

<400> SEQUENCE: 20

Leu Tyr Gly Val Asp Ser Ser Asn Ile Asp Asn Ala
1               5                   10

<210> SEQ ID NO 21
<211> LENGTH: 9
<212> TYPE: PRT
<213> ORGANISM: Artificial sequence
<220> FEATURE:
<223> OTHER INFORMATION: Monoclonal antibody fragment

<400> SEQUENCE: 21

Gly Ile Gly Phe Gly Tyr Tyr Tyr Tyr
1               5

<210> SEQ ID NO 22
<211> LENGTH: 9
<212> TYPE: PRT
<213> ORGANISM: Artificial sequence
<220> FEATURE:
<223> OTHER INFORMATION: Monoclonal antibody fragment

<400> SEQUENCE: 22

Ile Tyr Thr Gly Ile Ser Asp Ser Thr
1               5

<210> SEQ ID NO 23
<211> LENGTH: 21
<212> TYPE: PRT
<213> ORGANISM: Artificial sequence
<220> FEATURE:
<223> OTHER INFORMATION: Monoclonal antibody fragment

<400> SEQUENCE: 23

Ala Arg Ser Asp Pro Tyr Tyr Thr Thr Thr Tyr Thr Asn Thr Tyr Pro
1               5                   10                  15

Thr Tyr Trp Asn Leu
            20

<210> SEQ ID NO 24
<211> LENGTH: 6
<212> TYPE: PRT
<213> ORGANISM: Artificial sequence
<220> FEATURE:
<223> OTHER INFORMATION: Monoclonal antibody fragment

<400> SEQUENCE: 24

Gln Ser Ile Asn Asn Tyr
1               5

<210> SEQ ID NO 25
<211> LENGTH: 3
<212> TYPE: PRT
<213> ORGANISM: Artificial sequence
<220> FEATURE:
<223> OTHER INFORMATION: Monoclonal antibody fragment

<400> SEQUENCE: 25

Arg Ala Ser
1
```

```
<210> SEQ ID NO 26
<211> LENGTH: 14
<212> TYPE: PRT
<213> ORGANISM: Artificial sequence
<220> FEATURE:
<223> OTHER INFORMATION: Monoclonal antibody fragment

<400> SEQUENCE: 26

Gln Ser Tyr Tyr Tyr Ser Ser Ser Asn Asn Tyr Tyr Asn Ala
1               5                   10

<210> SEQ ID NO 27
<211> LENGTH: 8
<212> TYPE: PRT
<213> ORGANISM: Artificial sequence
<220> FEATURE:
<223> OTHER INFORMATION: Monoclonal antibody fragment

<400> SEQUENCE: 27

Gly Ile Asp Leu Ser Thr Tyr Ala
1               5

<210> SEQ ID NO 28
<211> LENGTH: 7
<212> TYPE: PRT
<213> ORGANISM: Artificial sequence
<220> FEATURE:
<223> OTHER INFORMATION: Monoclonal antibody fragment

<400> SEQUENCE: 28

Ile Asn Arg Ser Ser Lys Thr
1               5

<210> SEQ ID NO 29
<211> LENGTH: 14
<212> TYPE: PRT
<213> ORGANISM: Artificial sequence
<220> FEATURE:
<223> OTHER INFORMATION: Monoclonal antibody fragment

<400> SEQUENCE: 29

Gly Arg Val Met Ser Pro Tyr Ser Val Ala Gly Gly Asp Leu
1               5                   10

<210> SEQ ID NO 30
<211> LENGTH: 7
<212> TYPE: PRT
<213> ORGANISM: Artificial sequence
<220> FEATURE:
<223> OTHER INFORMATION: Monoclonal antibody fragment

<400> SEQUENCE: 30

Ser Asp Leu Ser Asp Tyr Thr
1               5

<210> SEQ ID NO 31
<211> LENGTH: 7
<212> TYPE: PRT
<213> ORGANISM: Artificial sequence
<220> FEATURE:
<223> OTHER INFORMATION: Monoclonal antibody fragment

<400> SEQUENCE: 31

Leu Arg Ser Asp Gly Ser Tyr
1               5
```

<210> SEQ ID NO 32
<211> LENGTH: 9
<212> TYPE: PRT
<213> ORGANISM: Artificial sequence
<220> FEATURE:
<223> OTHER INFORMATION: Monoclonal antibody fragment

<400> SEQUENCE: 32

Gly Leu Pro Tyr Ser Val Glu Tyr Val
1               5

<210> SEQ ID NO 33
<211> LENGTH: 117
<212> TYPE: PRT
<213> ORGANISM: Artificial sequence
<220> FEATURE:
<223> OTHER INFORMATION: Monoclonal antibody fragment

<400> SEQUENCE: 33

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Ser Ala Ser
            20                  25                  30

Tyr Tyr Ile Tyr Trp Val Arg Gln Ala Pro Gly Lys Gly Leu Glu Tyr
        35                  40                  45

Ile Ala Tyr Ile Thr Gly Asp Asp Asp Lys Arg Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Arg Asn Leu Pro Asp Glu Leu Trp Gly Pro Gly Thr Leu
            100                 105                 110

Val Thr Val Ser Ser
        115

<210> SEQ ID NO 34
<211> LENGTH: 117
<212> TYPE: PRT
<213> ORGANISM: Artificial sequence
<220> FEATURE:
<223> OTHER INFORMATION: Monoclonal antibody fragment

<400> SEQUENCE: 34

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Ser Ala Ser
            20                  25                  30

Tyr Tyr Ile Tyr Trp Val Arg Gln Ala Pro Gly Lys Gly Leu Glu Tyr
        35                  40                  45

Ile Ala Tyr Ile Thr Gly Asp Asp Asp Lys Arg Thr Tyr Tyr Ala Asn
    50                  55                  60

Trp Ala Lys Gly Arg Phe Thr Ile Ser Arg Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Arg Asn Leu Pro Asp Glu Leu Trp Gly Pro Gly Thr Leu
            100                 105                 110

Val Thr Val Ser Ser

<210> SEQ ID NO 35
<211> LENGTH: 112
<212> TYPE: PRT
<213> ORGANISM: Artificial sequence
<220> FEATURE:
<223> OTHER INFORMATION: Monoclonal antibody fragment

<400> SEQUENCE: 35

Asp Ile Gln Met Thr Gln Thr Pro Ser Thr Leu Ser Ala Ser Val Gly
1               5                   10                  15

Asp Arg Val Thr Ile Thr Cys Gln Ser Ser Glu Ser Val Tyr Ser Tyr
            20                  25                  30

Lys Asn Leu Ala Trp Tyr Gln Gln Lys Pro Gly Lys Pro Pro Lys Leu
        35                  40                  45

Leu Ile Trp Gln Ala Ser Arg Leu Ser Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gly Thr Tyr Tyr Ser
                85                  90                  95

Ser Ala Trp Asp Phe Val Phe Gly Gly Gly Thr Lys Val Glu Ile Lys
            100                 105                 110

<210> SEQ ID NO 36
<211> LENGTH: 112
<212> TYPE: PRT
<213> ORGANISM: Artificial sequence
<220> FEATURE:
<223> OTHER INFORMATION: Monoclonal antibody fragment

<400> SEQUENCE: 36

Gln Ala Gln Met Thr Gln Thr Pro Ser Thr Leu Ser Ala Ser Val Gly
1               5                   10                  15

Asp Arg Val Thr Ile Thr Cys Gln Ser Ser Glu Ser Val Tyr Ser Tyr
            20                  25                  30

Lys Asn Leu Ala Trp Tyr Gln Gln Lys Pro Gly Lys Pro Pro Lys Leu
        35                  40                  45

Leu Ile Trp Gln Ala Ser Arg Leu Ser Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gly Thr Tyr Tyr Ser
                85                  90                  95

Ser Ala Trp Asp Phe Val Phe Gly Gly Gly Thr Lys Val Glu Ile Lys
            100                 105                 110

<210> SEQ ID NO 37
<211> LENGTH: 122
<212> TYPE: PRT
<213> ORGANISM: Artificial sequence
<220> FEATURE:
<223> OTHER INFORMATION: Monoclonal antibody fragment

<400> SEQUENCE: 37

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Ser Ser Ser
            20                  25                  30

```
Tyr Trp Ile Cys Trp Val Arg Gln Ala Pro Gly Lys Gly Leu Glu Tyr
            35                  40                  45

Ile Gly Tyr Ile Trp Ser Gly Asn Gly Ala Thr Tyr Tyr Ala Ser Trp
 50                  55                  60

Ala Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Phe
                 85                  90                  95

Cys Ala Arg Asn Tyr Asp Ala Ser Gly Tyr Gly Ile Phe His Leu Trp
                100                 105                 110

Gly Pro Gly Thr Leu Val Thr Val Ser Ser
            115                 120
```

<210> SEQ ID NO 38
<211> LENGTH: 122
<212> TYPE: PRT
<213> ORGANISM: Artificial sequence
<220> FEATURE:
<223> OTHER INFORMATION: Monoclonal antibody fragment

<400> SEQUENCE: 38

```
Gln Val Gln Leu Val Glu Ser Gly Gly Gly Leu Val Gln Pro Gly Gly
 1               5                  10                  15

Ser Leu Arg Leu Ser Cys Ser Ala Ser Gly Phe Ser Phe Ser Ser Ser
            20                  25                  30

Tyr Trp Ile Cys Trp Val Arg Gln Ala Pro Gly Lys Gly Leu Glu Leu
            35                  40                  45

Ile Gly Tyr Ile Trp Ser Gly Asn Gly Ala Thr Tyr Tyr Ala Ser Trp
 50                  55                  60

Ala Lys Gly Arg Phe Thr Ile Ser Arg Asp Thr Ser Lys Asn Thr Val
 65                  70                  75                  80

Tyr Leu Gln Met Asn Ser Leu Arg Ala Glu Asp Thr Ala Val Tyr Phe
                 85                  90                  95

Cys Ala Arg Asn Tyr Asp Ala Ser Gly Tyr Gly Ile Phe His Leu Trp
                100                 105                 110

Gly Pro Gly Thr Leu Val Thr Val Ser Ser
            115                 120
```

<210> SEQ ID NO 39
<211> LENGTH: 111
<212> TYPE: PRT
<213> ORGANISM: Artificial sequence
<220> FEATURE:
<223> OTHER INFORMATION: Monoclonal antibody fragment

<400> SEQUENCE: 39

```
Asp Ile Gln Met Thr Gln Thr Pro Ser Ser Leu Ser Ala Ser Val Gly
 1               5                  10                  15

Asp Arg Val Thr Ile Asn Cys Gln Ala Ser Gln Ser Ile Val Ser Ser
            20                  25                  30

Tyr Leu Ser Trp Tyr Gln Gln Lys Pro Gly Lys Pro Pro Lys Leu Leu
            35                  40                  45

Ile Tyr Ser Ala Ser Lys Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Leu Tyr Gly Val Asp Ser Ser
```

85                  90                  95
Asn Ile Asp Asn Ala Phe Gly Gly Gly Thr Lys Val Glu Ile Lys
                100                 105                 110

<210> SEQ ID NO 40
<211> LENGTH: 111
<212> TYPE: PRT
<213> ORGANISM: Artificial sequence
<220> FEATURE:
<223> OTHER INFORMATION: Monoclonal antibody fragment

<400> SEQUENCE: 40

Ala Val Gln Met Thr Gln Thr Pro Ser Ser Leu Ser Ala Ser Val Gly
1               5                   10                  15

Asp Arg Val Thr Ile Asn Cys Gln Ala Ser Gln Ser Ile Val Ser Ser
            20                  25                  30

Tyr Leu Ser Trp Tyr Gln Gln Lys Pro Gly Lys Pro Pro Lys Leu Leu
        35                  40                  45

Ile Tyr Ser Ala Ser Lys Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Tyr Gly Val Asp Ser Ser
                85                  90                  95

Asn Ile Asp Asn Ala Phe Gly Gly Gly Thr Lys Val Glu Ile Lys
                100                 105                 110

<210> SEQ ID NO 41
<211> LENGTH: 32
<212> TYPE: DNA
<213> ORGANISM: Artificial sequence
<220> FEATURE:
<223> OTHER INFORMATION: Synthetic primer

<400> SEQUENCE: 41
cggcctctag agagctcgtg mtgacccaga ct                                     32

<210> SEQ ID NO 42
<211> LENGTH: 32
<212> TYPE: DNA
<213> ORGANISM: Artificial sequence
<220> FEATURE:
<223> OTHER INFORMATION: Synthetic primer

<400> SEQUENCE: 42
cggcctctag agagctcgat mtgacccaga ct                                     32

<210> SEQ ID NO 43
<211> LENGTH: 32
<212> TYPE: DNA
<213> ORGANISM: Artificial sequence
<220> FEATURE:
<223> OTHER INFORMATION: Synthetic primer

<400> SEQUENCE: 43
gcatccgtac gtcgtaggat ctccagctcg gt                                     32

<210> SEQ ID NO 44
<211> LENGTH: 32
<212> TYPE: DNA
<213> ORGANISM: Artificial sequence
<220> FEATURE:
<223> OTHER INFORMATION: Synthetic primer

```
<400> SEQUENCE: 44
gcatccgtac gtcgtttgat ttccacattg gt                                    32

<210> SEQ ID NO 45
<211> LENGTH: 32
<212> TYPE: DNA
<213> ORGANISM: Artificial sequence
<220> FEATURE:
<223> OTHER INFORMATION: Synthetic primer

<400> SEQUENCE: 45
gcatccgtac gtcgtttgac saccacctcg gt                                    32

<210> SEQ ID NO 46
<211> LENGTH: 31
<212> TYPE: DNA
<213> ORGANISM: Artificial sequence
<220> FEATURE:
<223> OTHER INFORMATION: Synthetic primer

<400> SEQUENCE: 46
acaagtctag agagctcgtg ctgactcagt c                                     31

<210> SEQ ID NO 47
<211> LENGTH: 30
<212> TYPE: DNA
<213> ORGANISM: Artificial sequence
<220> FEATURE:
<223> OTHER INFORMATION: Synthetic primer

<400> SEQUENCE: 47
catccgtacg tcggcctgtg acggtcagct                                       30

<210> SEQ ID NO 48
<211> LENGTH: 32
<212> TYPE: DNA
<213> ORGANISM: Artificial sequence
<220> FEATURE:
<223> OTHER INFORMATION: Synthetic primer

<400> SEQUENCE: 48
cttccctcga gcagtcggtg gaggagtccr gg                                    32

<210> SEQ ID NO 49
<211> LENGTH: 32
<212> TYPE: DNA
<213> ORGANISM: Artificial sequence
<220> FEATURE:
<223> OTHER INFORMATION: Synthetic primer

<400> SEQUENCE: 49
cttccctcga gcagtcggtg aaggagtccg ag                                    32

<210> SEQ ID NO 50
<211> LENGTH: 32
<212> TYPE: DNA
<213> ORGANISM: Artificial sequence
<220> FEATURE:
<223> OTHER INFORMATION: Synthetic primer

<400> SEQUENCE: 50
cttccctcga gcagtcgytg gaggagtccg gg                                    32

<210> SEQ ID NO 51
```

```
<211> LENGTH: 32
<212> TYPE: DNA
<213> ORGANISM: Artificial sequence
<220> FEATURE:
<223> OTHER INFORMATION: Synthetic primer

<400> SEQUENCE: 51
cttccctcga gcagsagcag ctgrtggagt cc                              32

<210> SEQ ID NO 52
<211> LENGTH: 40
<212> TYPE: DNA
<213> ORGANISM: Artificial sequence
<220> FEATURE:
<223> OTHER INFORMATION: Synthetic primer

<400> SEQUENCE: 52
catcgggccc ttggtggagg ctgargagay ggtgaccagg                      40
```